United States Patent [19]
Tsuchiya et al.

[11] Patent Number: 5,640,247
[45] Date of Patent: Jun. 17, 1997

[54] METHOD FOR MEASURING INTERNAL INFORMATION IN A SCATTERING MEDIUM AND APPARATUS FOR THE SAME

[75] Inventors: Yutaka Tsuchiya; Kazuyoshi Ohta; Tsuneyuki Urakami, all of Hamamatsu, Japan

[73] Assignee: Hamamatsu Photonics K.K., Hamamatsu, Japan

[21] Appl. No.: 353,202

[22] Filed: Dec. 1, 1994

[30] Foreign Application Priority Data

Dec. 1, 1993 [JP] Japan .................................. 5-301979
Apr. 21, 1994 [JP] Japan .................................. 6-083489

[51] Int. Cl.[6] .......................... G01N 21/47; G01N 21/00; A61B 5/00; A61B 6/00
[52] U.S. Cl. .......................... 356/446; 356/73; 128/633; 128/664; 128/665
[58] Field of Search .................... 356/41, 338, 340, 356/343, 434–435, 446–447, 73; 128/664–665, 633

[56] References Cited

U.S. PATENT DOCUMENTS

| 4,286,602 | 9/1981 | Guy ................................. 128/665 |
| 4,407,290 | 10/1983 | Wilber .............................. 356/41 |
| 4,600,011 | 7/1986 | Watmough ......................... 128/665 |
| 5,057,695 | 10/1991 | Hirao et al. ....................... 356/41 |
| 5,277,181 | 1/1994 | Mendelson et al. ............... 356/41 |

FOREIGN PATENT DOCUMENTS

| 06129984 | 5/1994 | Japan . |
| 8912223 | 12/1989 | WIPO . |
| 9300045 | 1/1993 | WIPO . |

OTHER PUBLICATIONS

Patterson et al. "Time Resolved Reflectance and Transmittance for the Non-Invasive Measurement of Tissue Optical Properties", Applied Optics, vol. 28, No. 12, Jun. 15 1989, pp. 2331–2336.

Wilson et al, "Optical Reflectance and Transmittance of Tissues: Principles and Applications", IEE Journal of Quantam Electronics, vol. 26, No. 12, Dec. 1990, pp. 2186–2199.

Patterson et al, "Applications of Time–Resolved Light Scattering Measurements to Photodynamic Therapy Dosimetry", SPIE, vol. 1203 Phtotdynamic Therapy Mechanism II (1990), pp. 62–75.

Flock et al, "Monte Carlo Modeling of Light Propagation in Highly Scattering Tissues— I: Model Predictions and Comparison with Diffusion Therapy", IEEE Transactions on Biomedical Engineering, vol. 36, No. 12, pp. 1162–1168.

Sevick et al, "Time–Dependent Photon Migration Imaging", SPIE, vol. 1599 Recent Advances in the Uses of Light in Physics, Chemistry, Engineering and Medicine (1991), pp. 273–283.

Sevick et al, "Quantitation of Time–and Frequency–Resolved Optical Spectra for the Determination of Tissue Oxygenation", Analytical Biochemistry 195 (1991), pp. 330–351.

Jacques, "Time–Resolved Reflectance Spectroscopy in Turbid Tissues", IEEE Transactions on Biomedical Engineering, vol. 36, No. 12, dec. 1989, pp. 1155–1161.

(List continued on next page.)

Primary Examiner—Frank G. Font
Assistant Examiner—Jason D. Vierra Eisenberg
Attorney, Agent, or Firm—Cushman Darby & Cushman, IP Group of Pillsbury Madison & Sutro, LLP

[57] ABSTRACT

Light having a predetermined wavelength and various incident angle components to be incident on a surface of a scattering medium to generate an equivalent point light source or a group of equivalent point light sources near or on the surface of the scattering medium, and light diffused during propagation in the scattering medium is detected outside, and considering isotropic light from the equivalent light sources is immediately diffused, the optically detected signal is processed to detect a predetermined parameter which is primary information and this predetermined parameter is processed to measure internal information which is secondary information in the scattering medium with high accuracy.

25 Claims, 22 Drawing Sheets

CONFIGURATION OF APPARATUS OF THE FIRST EMBODIMENT

OTHER PUBLICATIONS

Arridge et al, "The Theoretical Basis for the Determination of Optical Pathlengths in Tissue: Temporal and Frequency Analysis", Phys. Med. Biol., 1992, vol. 37, No. 7, pp. 1531–1560.

Wilson et al, "Time–Dependent Optical Spectroscopy and Imaging for Biomedical Applications", Proceedings of the IEEE, vol. 80, No. 6, Jun. 1992, pp. 918–930.

Schmitt et al, "Interference of Diffusive Light Waves", J. Opt. Soc. Am. A, vol. 9, No. 10, Oct 1992, pp. 1832–1843.

Madsen et al, "Experimental Tests of a Simple Diffusion Model for the Estimation of Scattering and Absorption Coefficients of Turbid Media From Time–Resolved Diffuse Reflectance Measurements", Applied Optics, vol. 31, No. 18 Jun. 20, 1992, pp. 3509–3517.

MODEL FOR OBTAINING PHOTON FLUENCE RATE (φ)
IN SCATTERING MEDIUM (CONVENTIONAL EXAMPLE)

BEHAVIOR OF LIGHT IN SCATTERING MEDIUM WITH
RESPECT TO COLLIMATED LIGHT INCIDENCE
(CONVENTIONAL EXAMPLE)

PHOTON FLUENCE RATE($\phi$) NEAR FREE SURFACE

REFLECTION MEASUREMENT MODEL

MEASUREMENT OF ABSOLUTE VALUE OF INTERNAL INFORMATION

MEASUREMENT OF ABSOLUTE VALUE OF
INTERNAL INFORMATION

CONFIGURATION OF MEASURING HEAD UNIT OF APPARATUS OF THE SECOND EMBODIMENT

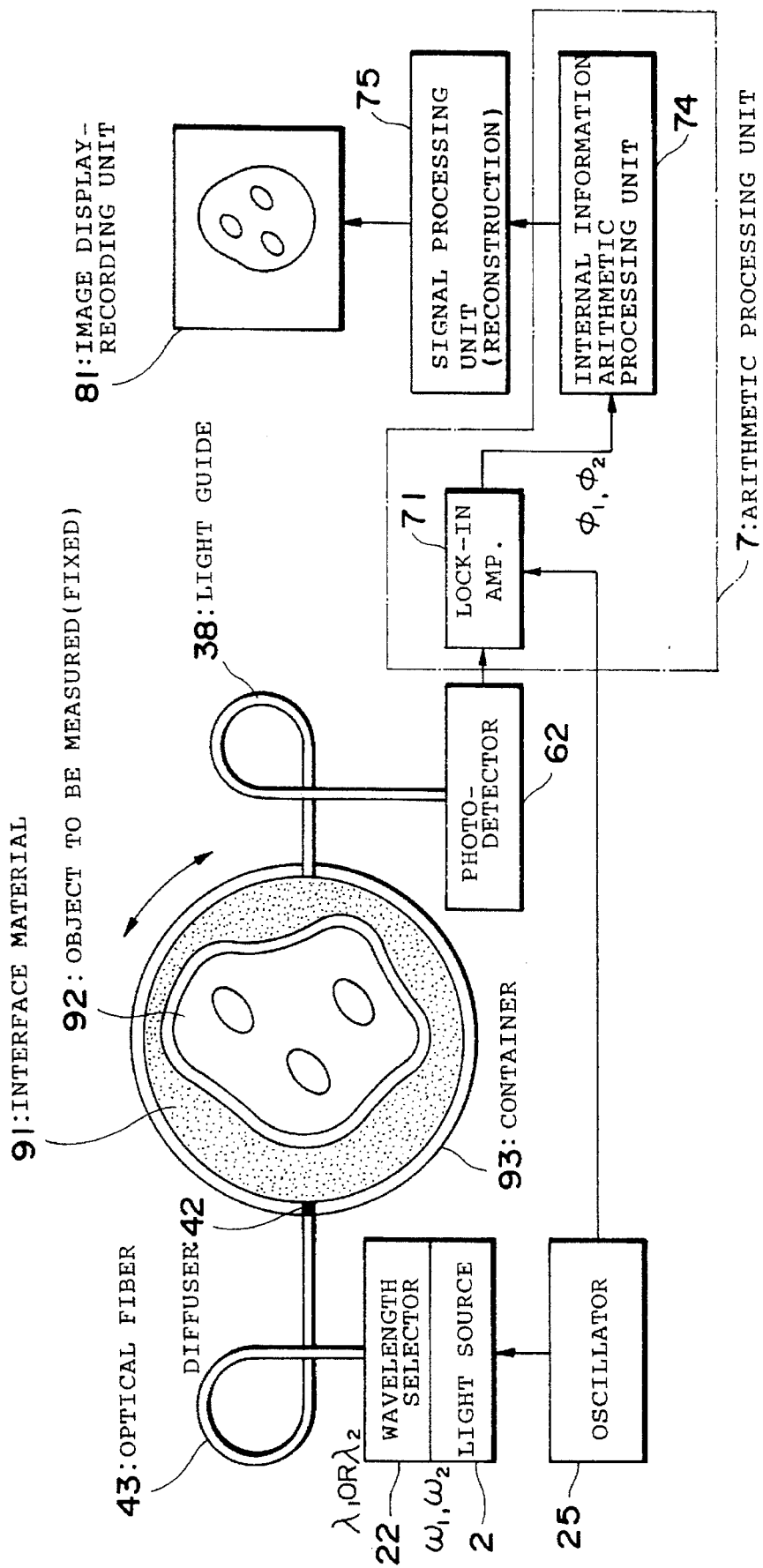

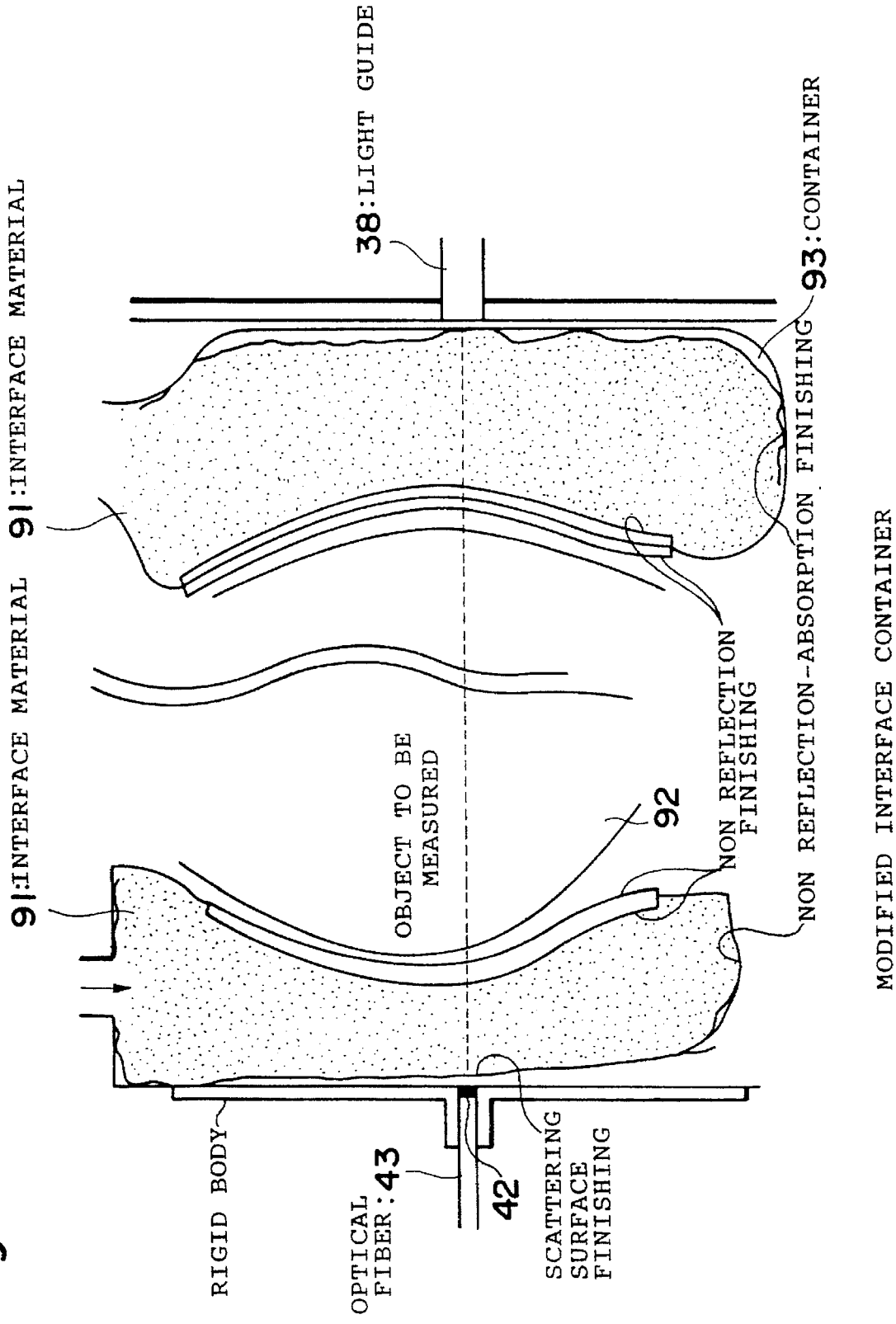

METHOD FOR MEASURING INTERNAL INFORMATION IN A SCATTERING MEDIUM AND APPARATUS FOR THE SAME

BACKGROUND OF THE INVENTION

1. Field of the Invention

The present invention relates to non-invasive measurement of internal information in a scattering medium by causing light having various incident angle components to be incident on the scattering medium, and detecting light diffused during propagation in the scattering medium. More particularly, this invention relates to a method for measuring internal information in a scattering medium and an apparatus for the same, which are capable of measuring absolute values of an absorption coefficient and a transport scattering coefficient of the scattering medium, absolute quantities of a specific absorptive constituent and a specific scattering constituent, a degree of oxygen saturation of hemoglobin, their time changes, their spatial distributions etc. and which are capable of improving measurement accuracy.

2. Related Background Art

Demands for precise measurement of an absorption coefficient, a scattering coefficient and a transport scattering coefficient in a scattering medium such as a living body, the concentration of a specific absorptive constituent, an absolute quantity of a specific absorptive constituent, their time changes, and their spacial distributions have been very strong. There are several attempts therefore to achieve this such as a method using continuous light, or modulated light (e.g., pulsed light, square wave light, sinusoidal wave modulated light etc.), and a method using lights having different wavelengths (e.g., dual wavelength spectroscopy). It has been known that the behavior of light diffused during propagation in the scattering medium can be analyzed, experimented and examined in accordance with Monte Carlo calculation using a computer, and can be described and analyzed with photon diffusion theory. Present conditions with regard to measurement of a scattering medium are described in detail, for example, in the following references 1)–6) (note that hereinafter, the references will be referred to with a reference number X) or a superscript $^{X)}$ in sentences).

References

1) B. C. Wilson and S. L. Jacques: Optical Reflectance and Transmittance of Tissues: Principle and Application, IEEE J. Quatum Electron. Vol. 26, No. 12, pp. 2186–2199 (1990)

2) M. S. Patterson, J. D. Moulton, B. C. Wilson, and B. Chance: Application of Time-Resolved Light Scattering Measurements to Photodynamic Theraphy Dosimetry, Proc. SPIE, Vol. 1203, p.62–75 (1990)

3) E. M. Sevick, N. G. Wang, and B. Chance: Time-dependent Photon Migration Imaging, Proc. SPIE, Vol. 1599, p.273–283 (1991)

4) E. M. Sevick, B. Chance, J. Leigh, S. Nioka, and M. Marls: Quantitation of Time-and Frequency-Resolved Optical Spectra for the Determination of Tissue Oxygeneration, Analytical Biochemistry Vol. 195, p. 330–351 (1991)

5) M. S. Patterson, B. Chance, and B. C. Wilson: Time Resolved Reflectance and Transmittance for the Non-Invasive Measurement of Tissue Optical Properties, Applied Optics, Vol. 28, No. 12, pp. 2331–2336 (1989)

6) S. T. Flock, M. S. Patterson, B. C. Wilson and D. R. Wyman: Monte Carlo Modeling of Light Propagation in Highly Scattering Tissues-I: Model Predictions and Comparison with Diffusion Theory, IEEE trans. Biomedical Eng., Vol. 36, No. 12, pp. 1162–1168 (1989)

However, in the above conventional techniques, there is a serious problem that sufficient measurement accuracy cannot be obtained regardless of the type of methods and devices are used[1-4].

Here, as reading the above conventional techniques, it will be understood that a method and an apparatus reported in the reference 5) or a method and apparatus[2-4] based upon this method and apparatus show relatively high measurement accuracy. However, these conventional techniques cause collimated light or almost collimated light to be incident on the scattering medium, and such light incident condition is a direct cause or indirect cause of limiting the measurement accuracy, which is a serious problem in the conventional techniques. In order to make an understanding of an object and novelty of the present invention easier, a method and an apparatus reported in the above reference 5) or a method and an apparatus in conformity with these method and apparatus, which are considered to be superior in measurement accuracy to the other conventional techniques, will be described below as an example. Keeping in mind that one of the features of the present invention is causing light having various incident angle components to be incident on the scattering medium, which will be described later, the reader should readily understand the following description. There are no such reports that a measurement method and an apparatus utilizing incident light other than collimated light are examined and analyzed in this field and conventional techniques.

It has been known that the behavior of light diffused during propagation in the scattering medium can be precisely described and analyzed with a Photon Diffusion theory. In other words, by solving a photon diffusion equation which is derived from an approximation of the photon transport theory, we can know the behavior of light which is scattered, absorbed and diffused during propagation in the scattering medium. However, for a finite scattering medium, the photon diffusion equations need to be solved with a boundary condition. The boundary condition is that there is no incidence of diffused light from outside of the scattering medium at the boundary because there is no light diffusion outside the scattering medium.

Patterson et al. developed a model including this boundary condition, and derived a solution of the photon diffusion equation under the boundary condition given by the model, that is, a photon fluence rate $\phi$, and then reported that temporal waveform (equivalent to a flight time distribution of photon as will be described later) of photon current J derived from the photon fluence rate $\phi$ was substantially matched with the results obtained with Monte Carlo calculation or actual experimental values[5]. This model is the one shown in FIG. 1, and the following conditions, assumptions, approximation and a point light source of negative polarity are introduced[5]. Note that the photon fluence rate $\phi$, photon current density J etc. will be described in detail later.

(1) Incident light is thin collimated light, and normally incident on a scattering medium.

(2) It is assumed that incident light or photon travels a distance $z_0'$ in a straight line without influence of scattering and that thereafter light diffusion is started.

(3) It is assumed that the photon fluence rate $\phi$ is zero at a surface (called free surface) of a scattering medium.

(4) In order to satisfy the above boundary condition, a point light source of negative polarity is placed on a position $z_0$ outside a surface of a scattering medium.

(5) It is assumed that the photon current density J at a free surface is proportional to the gradient of the photon fluence rate φ at the free surface (called Fick's law).

A detailed description of this method follows. They considered that light incident perpendicular to the surface of scattering medium travels $Z_0'$ in a straight line without influence of scattering and thereafter light diffusion is started, and modeled this phenomenon with a point light source placed on a position $Z_0'$ within the scattering medium. Next, in order to satisfy the above-described boundary condition (i.e., φ=0 at a free surface), it was assumed that a point light source of negative polarity was on a position $Z=-Z_0'$ on a z-axis outside the scattering medium. Then, a solution of the photon diffusion equation under the boundary condition, that is, the photon fluence rate φ was derived. Next, as the photon current density J followed the Fick's law, the photon current density J flowing from the surface of the scattering medium was obtained from the gradient of the photon fluence rate φ at the free surface. Note that a light source of positive polarity radiates light in all directions. The light source of negative polarity is a virtual point light source having opposite characteristics of the point light source of positive polarity and considered to radiate light of negative intensity in all directions.

Further, they examined the above model and the results obtained therefrom and concluded that a value of $Z_0'$ is equal or nearly equal to the mean free path, that is, $1/\mu_s'$. Note that $\mu_s'$ is a transport scattering coefficient. They also examined the model for the measurement of light transmitting a slab-like scattering medium in the same way as above and introduced the same $Z_0'$ as above.

Their knowledge had been applied to various measurements in the field of tissue spectroscopy but sufficient measurement accuracy has not been achieved yet, which was described at the beginning.

SUMMARY OF THE INVENTION

The present invention is to solve the above-described problems in the conventional techniques, to significantly improve the measurement accuracy and to achieve the measurement of the absolute value of various parameters in the scattering medium. The problems in the conventional techniques will be analyzed to improve the measurement accuracy significantly, and as compared with this, detailed problems to be solved by the present invention will be explained below.

Light is scattered, absorbed and diffused at random during propagation in a scattering medium and spreads over almost all of the scattering medium. Some light components emerge at the surface of the scattering medium. When this light diffused during propagation is detected by a photodetector placed on a surface of the scattering medium, trajectries of photons to be detected by a photodetector maybe schematically shown, as in FIG. 2. That is, FIG. 2 schematically shows trajectries of photons to be utilized (to be incident on the photodetector) in the actual measurement. In this case, the incident light is collimated light, and $Z_0'$ in FIG. 2 is the $Z_0'$ proposed by Patterson et al. Note that at the present, in strict sense, it has been apparent from the examination of the inventors of the present application that $Z_0' \neq 1/\mu_s'$. In FIG. 2, a reflection measurement method which is to detect light at a position $P_1(\rho, 0)$ and a transmission measurement method which is to detect light at a position $P_2(0, z)$ are also shown.

Such behavior of photons does not relate to time change in incident light intensity, that is, light intensity of incident light, so that even though incident light is pulsed light, square wave light, or modulated light, their behavior will not alter. For example, FIG. 3 shows a state in which sinusoidal wave modulated light is incident on a scattering medium and light diffused during propagation in the scattering medium is received, and signals only having modulated frequency components are extracted from detected signals to measure internal information of the scattering medium. As shown in FIG. 3, point light sources of positive and negative polarities are also placed at $z_0'$ and $-z_0'$, respectively.

Based upon the above description, the problems in the conventional techniques will be enumerated below. First, the assumption that $Z_0'=1/\mu_s'$ or $z_0' \approx 1/\mu_s'$ does not hold. This limits the measurement accuracy of the conventional techniques, and for high measurement accuracy, this assumption does not hold because of the following reasons.

Prior to the present invention, the inventors of the present application precisely analyzed, experimented and examined the behavior of light in the scattering medium, and found that precisely, $z_0' \neq 1/\mu_s'$ and that $z_0'$ depended on the light incident conditions. It was found that an error caused by the assumption $z_0'=1/\mu_s'$ was not only the problem in the error of photon fluence rate φ but also the serious problem in the error of absorption coefficient or transport scattering coefficient of the scattering medium obtained from the photon fluence rate φ with a method to be described later. In a strict sense, the above-described results reported by Patterson et al. do not match with the results of Monte Carlo calculation by the inventors of the present application. It was confirmed that the Monte Carlo calculation by the inventors of the present application well matched with the actual experimental results. Consequently, in a strict sense, the results reported by Patterson et al. do not match with the actual experimental results.

It was apparent that the method reported by Patterson et al. and a method and an apparatus for measuring internal information in a scattering medium based on this method had quite large measurement error. Accordingly, it was apparent that in order to improve the measurement accuracy, a precise photon diffusion equation and solution, or development of new model would be needed.

As apparent from papers of Patterson et al., the second problem is that the above-described $z_0'$ is different for various kinds of scattering media having different scattering coefficients. That is, $z_0$ is equal to or nearly equal to $1/\mu_s'$ which is an inverse of a transport scattering coefficient of a scattering medium. Consequently, $z_0'$ takes various values for various kinds of scattering media.

Accordingly, in order to improve the measurement accuracy for various kinds of scattering media, $z_0'$ of each scattering medium needs to be precisely obtained by a different method. However, to obtain the above-described $z_0'$ means to measure a scattering medium with high accuracy, i.e., to measure $\mu_s'$ precisely, which is the overall objective. After all, in the conventional techniques, to improve the measurement accuracy of the scattering medium is hard.

The third problem is that the distribution of optical path density on the light incidence side and on the light detection side, of light diffused during propagation in a scattering medium is asymmetric. This is because light travels $z_0'$ in a straight line immediately after light is incident. Accordingly, distortion of optical path density of light diffused during propagation which is a cause of asymmetry appears clearly on a position near a light incident position, that is, a position $0<z<z_0'$, which will be described later.

In general, to treat such asymmetry property is not easy, and makes calculation or algorithm for measurement of an absolute quantity of a specific constituent in a scattering medium complicated. However, if some kind of approximation is used in order to avoid this complication, measurement error is made larger. Further, in the case of the measurement of a spacial distribution, e.g., of a specific absorptive constituent, if there is an asymmetry property, calculations relating to measurement of position and algorithm will be very complicated, which is an indirect cause of large measurement error. Thus, the third problem is a serious and complicated problem especially for imaging the inside of a scattering medium, the measurement of special distribution, and measurement of cross sectional image. Therefore, improvement is strongly desired.

Objects of the present invention are to improve the measurement accuracy of internal information measurement of a scattering medium in the field of industrial use, to measure an absolute value of internal information of a scattering medium, and to measure time change in internal information and spacial distribution with high accuracy.

The present invention causes light having various incident angle components to be incident on a surface of a scattering medium to generate an equivalent point light source or a group of equivalent point light sources near or on the surface of the scattering medium, and measures internal information in the scattering medium using light from the equivalent light source. The light incident conditions for the various kinds of scattering media are fixed and the position of the equivalent light source generated near the surface of the scattering medium can be specified. Moreover, the optical path distributions of the light diffused during propagation on the light incident side and photodetection side are symmetric. Therefore, the internal information in various scattering media can be measured with high accuracy.

A method for measuring a scattering medium of the present invention comprises (a) making light having various incident angle components and a predetermined wavelength to be incident on a scattering medium, (b) detecting the light having the predetermined wavelength, diffused during propagation in the scattering medium, at a position different from a light incident position to obtain an optically detected signal, (c) processing the optically detected signal to detect a predetermined parameter, the predetermined parameter being primary information relating to a scattering characteristic and an absorption characteristic on a diffusion-propagation path, and (d) processing the predetermined parameter based on a relation between a scattering characteristic and an absorption characteristic corresponding to the light having the predetermined wavelength on the diffusion-propagation path, and the predetermined parameter to calculate internal information in the scattering medium, the internal information being secondary information.

(1) The light having the predetermined wavelength can be a plurality of lights having a plurality of wavelengths, each having a different absorption coefficient to a specific constituent of the scattering medium. (2) The optically detected signal can be a plurality of signals obtained corresponding to light having predetermined wavelengths. (3) The predetermined parameter which is the primary information can be a plurality of parameters detected by processing each the optically detected signals. and (4) The relation can be simultaneous relations between a scattering characteristic and an absorptive characteristic corresponding to each light component having predetermined wavelength on the diffusion-propagation path, and the predetermined parameters.

Alternatively, (1) the optically detected signal can be a plurality of signals obtained by detecting light having predetermined wavelengths and diffused during propagation on the diffusion-propagation path in the scattering medium corresponding to a plurality of different distances between the light incident position and the photodetection point, (2) the predetermined parameter which is the primary information can be a plurality of parameters detected by processing each optically detected signal, and (3) the relation can be simultaneous relations between a scattering characteristic and an absorptive characteristic corresponding to the light having the predetermined wavelength on the diffusion-propagation path, and the predetermined parameters.

Moreover, the light having the predetermined wavelength can be modulated light. (1) The light having the predetermined wavelength can be modulated light having a predetermined modulated frequency component, and (2) the predetermined parameter which is the primary information can be a phase delay of a signal having a predetermined frequency component detected by processing the optically detected signal. Alternatively, (1) the light having the predetermined wavelength can be a plurality of modulated lights, each having a different modulated frequency component, (2) the optically detected signal can be a plurality of signals obtained corresponding to each the modulated light having the predetermined modulated frequency component, (3) the predetermined parameter which is the primary information can be a plurality of phase delays of the signals having the predetermined modulated frequency components detected by processing each the optically detected signals, and (4) the relation can be simultaneous relations between a scattering characteristic and an absorptive characteristic corresponding to each the modulated light having the predetermined modulated frequency component and the predetermined wavelength on the diffusion-propagation path, and the predetermined parameters.

The predetermined parameter which is the primary information can be (1) a quantity of light, (2) a delay time of the optically detected signal corresponding to light incidence, (3) a differential coefficient of a time-waveform of the optically detected signal, or (4) an amplitude of a signal having the same frequency component as the modulated light, included in the optically detected signals. Further, (1) the modulated light having the predetermined wavelength can be a plurality of modulated lights, each having a different predetermined modulated frequency component, (2) the optically detected signal can be a plurality of signals obtained corresponding to each the modulated light having the predetermined modulated frequency component, (3) the predetermined parameter which is the primary information can be a plurality of amplitudes of each signal having the predetermined modulated frequency component detected by processing the optically detected signal, and (4) the relation can be simultaneous relations between a scattering characteristic and an absorptive characteristic corresponding to each the modulated light having the predetermined modulated frequency component and the predetermined wavelength on the diffusion-propagation path, and the predetermined parameters.

An apparatus for measuring a scattering medium of the present invention comprises (a) a light source for generating light having a predetermined wavelength, (b) light-incident means for causing the light having the predetermined wavelength to have incident angle components in various directions and making the light to be incident on a scattering medium, (c) photodetecting means for detecting the light having the predetermined wavelength diffused during propagation in the scattering medium at a position different from a light incident position to obtain an optically detected signal, (d) parameter arithmetic processing means for processing the optically detected signal to detect a predetermined parameter which is primary information relating to a scattering characteristic and an absorption characteristic on a diffusion-propagation path, and (e) internal information arithmetic processing means for processing the predetermined parameter based on a relation between a scattering characteristic and an absorption characteristic corresponding to the light having the predetermined wavelength on the diffusion-propagation path, and the predetermined parameter to calculate internal information in the scattering medium, the internal information being secondary information.

Here, (1) the light source can generate a plurality of light component, each having a predetermined wavelength and a different absorption coefficient to a specific constituent in the scattering medium, (2) the photodetecting means can obtain the optically detected signal corresponding to each light component having the predetermined wavelength, (3) the parameter processing means can process each optically detected signal to detect a plurality of the predetermined parameters which are the primary information, and (4) the internal information arithmetic processing means can process the predetermined parameters based on simultaneous relations between a scattering characteristic and an absorption characteristic corresponding to each light component having the predetermined wavelength on the diffusion-propagation path, and the predetermined parameters to calculate internal information which is the secondary information in the scattering medium.

Moreover, (1) the number of the light-incident means and the photodetecting means can be plural, and plural light-incident means and plural the photodetecting means can be placed corresponding to a plurality of different distances between the light incident position and the photodetection point, (2) the photodetecting means can detect each light component having the predetermined wavelength diffused during propagation on the diffusion-propagation path in the scattering medium corresponding to each the distance between the light incident position and the photodetection point to obtain a plurality of optically detected signals, (3) the parameter arithmetic processing means can process each the optically detected signal to detect a plurality of predetermined parameters which is primary information, and (4) the internal information arithmetic processing means can process the predetermined parameters based on simultaneous relations between a scattering characteristic and an absorption characteristic corresponding to each light component having the predetermined wavelength on the diffusion-propagation path, and the predetermined parameters to calculate internal information which is the secondary information in the scattering medium.

The light source can be a light source for generating modulated light having a predetermined wavelength. In this case, (1) the light source can generate modulated light having a predetermined wavelength and a predetermined modulated frequency component, (2) the photodetecting means can detect the light having the predetermined wavelength and the predetermined modulated frequency component to obtain an optically detected signal, and (3) the parameter processing means can process the optically detected signal corresponding to the predetermined frequency component to detect a phase delay of the signal having the predetermined modulated frequency component which is the primary information.

Alternatively, (1) the light source can generate a plurality of modulated light components, each having a predetermined wavelength and a different predetermined modulated frequency component, (2) the photodetection means can detect each light component having the predetermined wavelength and the predetermined modulated frequency to obtain a plurality of optically detected signals, (3) the parameter arithmetic processing means can process each optically detected signal to detect a phase delay of each signal having the predetermined modulated frequency which is the primary information, and (4) the internal information arithmetic processing means can process the phase delays based on simultaneous relations between a scattering characteristic and an absorption characteristic corresponding to each the modulated light having the predetermined modulated frequency and the predetermined wavelength on the diffusion-propagation path, and the phase delays to calculate internal information which is the secondary information in the scattering medium.

According to the present invention, light having a predetermined wavelength and various incident angles is caused to be incident on a surface of a scattering medium to generate an equivalent point light source or a group of equivalent point light sources near or on the surface of the scattering medium. This equivalent point light source generates almost isotropic light. Assuming light from the light source is diffused immediately, an optically detected signal is processed to detect a predetermined parameter which is primary information, and the parameter is processed. Then, the measurement of internal information which is secondary information in the scattering medium can be measured with high accuracy. In this case, the predetermined parameter is photon current (equivalent to an optically detected signal), a time-change (differential value) in photon current, a time integral value of photon current, an average optical pathlength, an amplitude or a phase delay, of a specific frequency component included in the optically detected signal etc. and the internal information is absolute values of an absorption coefficient and a transport scattering coefficient, absolute values of a specific absorptive constituent and a specific scattering constituent, an absolute value of degree of oxygen saturation of hemoglobin, in the scattering medium, and their time change, spatial distribution, cross sectional image etc. Further, the arithmetic process to obtain the secondary information is processing the predetermined parameters to obtain the internal information in the scattering medium based on the relations between the predetermined parameters and the scattering characteristic and the absorptive characteristic on the diffusion-propagation path when light having a predetermined wavelength is diffused during propagation in the scattering medium. At this time, a plurality of light components having a predetermined wavelength can be utilized. In this case, the simultaneous relations corresponding to each light having a predetermined wavelength is utilized.

In the present invention internal information in the scattering medium is measured using light diffused during propagation generated as described above, and arithmetic relationships are used to obtain secondary information. These relationships include relationships between predetermined parameters, and between the scattering characteristic and the absorption characteristic on the diffusion and propagation path when the light having a predetermined wavelength is diffused during propagation in the scattering medium. Errors caused by approximation and assumption, which causes problems in the conventional techniques, by limiting the measurement accuracy can significantly be decreased, the light incident conditions for various kinds of scattering media can be fixed, the position of the equivalent light source generated near the surface of the scattering medium can precisely be specified, and the optical path distributions of light diffused during propagation on the light incident side and the light emerging side can be made symmetric. Therefore, the measurement accuracy for the internal information in the scattering medium, which is the secondary information, can significantly be improved. Further, the measurement of absolute values of internal information in the scattering medium, the improvement of measurement accuracy, and the highly precise measurement of time-change and spatial distribution can be made possible.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

FIG. 25 is a view showing a configuration of an apparatus of the fifth embodiment.

FIG. 26 is a view illustrating a modified example of an interface container.

DETAILED DESCRIPTION OF THE PREFERRED EMBODIMENTS

Prior to the description of the embodiments of the present invention, a principle of the present invention will be described.

Principle of the Present Invention

1. Incidence of Light Having Various Incident Angle Components on Scattering Medium One of features of the present invention is to cause light having various incident angle components to be incident on a scattering medium. First, the effects of this feature will be explained below.

The behavior of each photon diffused during propagation in a scattering medium can be analyzed and examined according to Monte Carlo Calculation using a computer. It has been known that the results of the Monte Carlo Calculation match well with the experimental results using a physical model or a living body. Then, the inventors of the present application experimented on, examined and analyzed the behavior of light when light having various incident angle components on a scattering medium.

Figure 1:
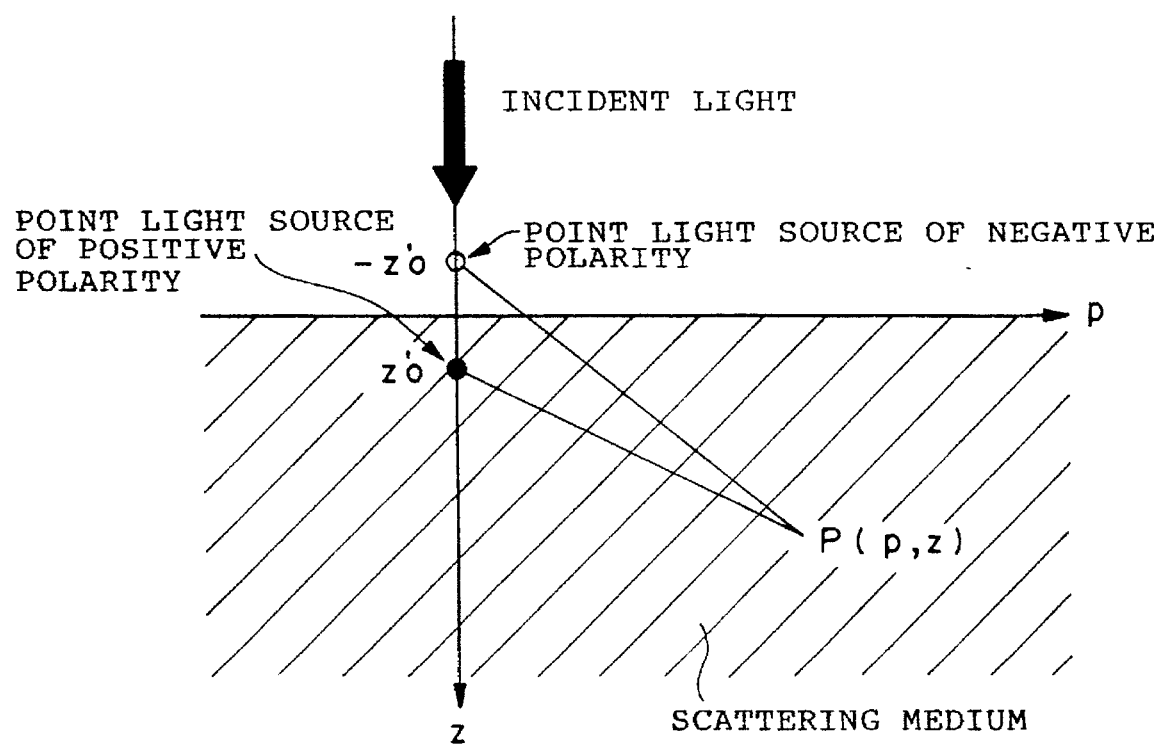
FIG. 1 is a view illustrating a model (conventional) to obtain a photon fluence rate φ in a scattering medium.
Figure 2:
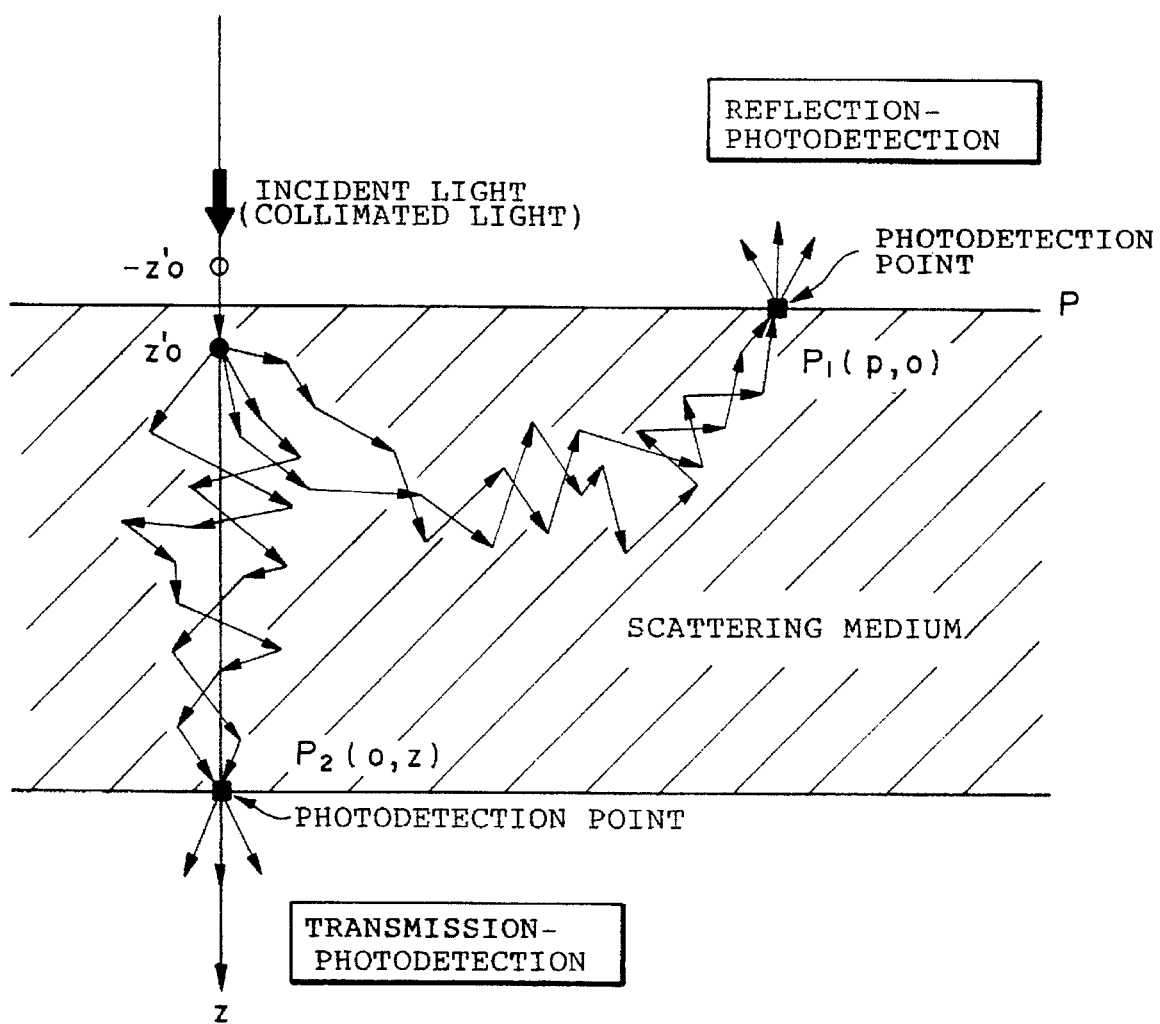
FIG. 2 is a view (conventional) illustrating the behavior of light in a scattering medium upon incidence of collimated light.
Figure 3:
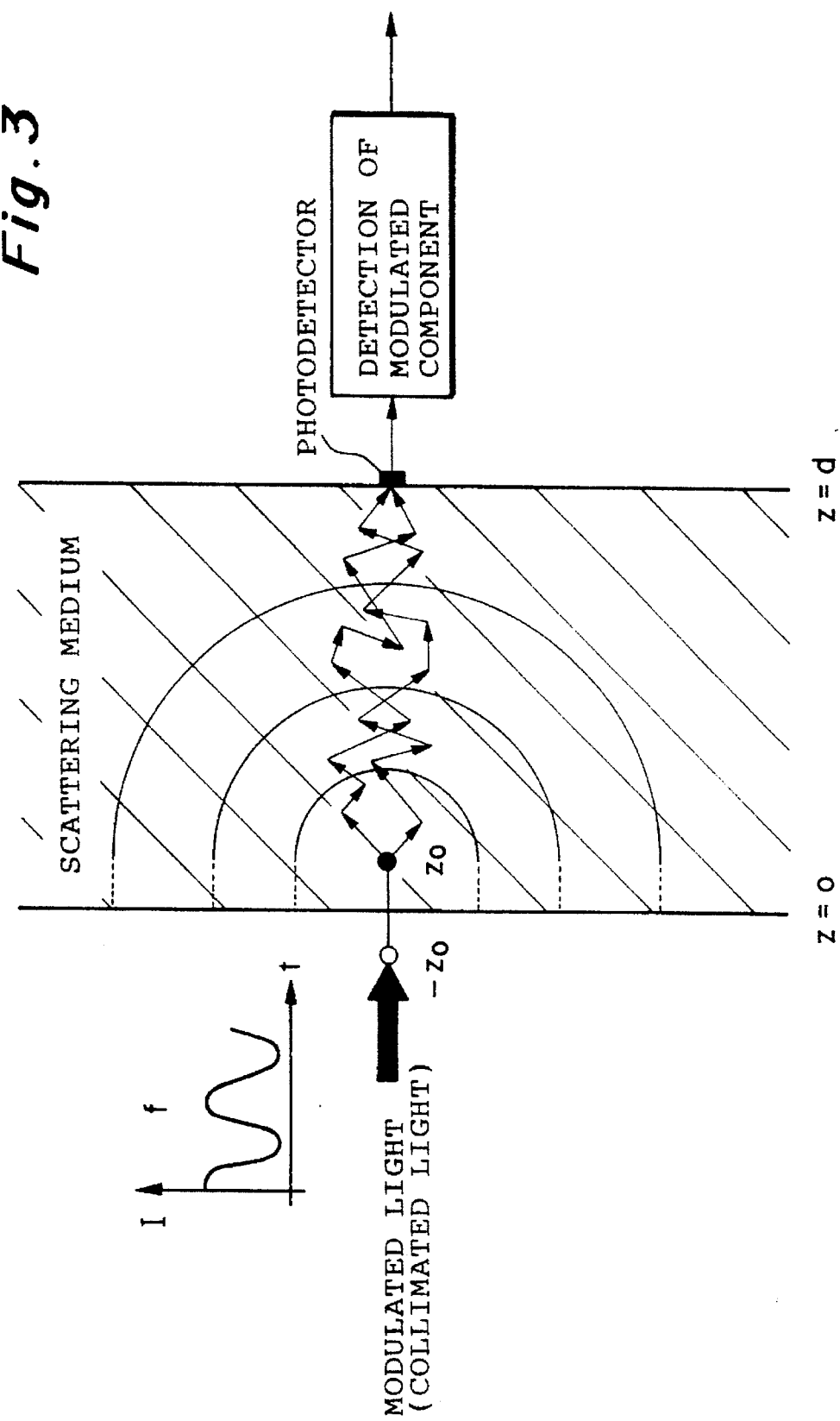
FIG. 3 is a view (conventional) illustrating the behavior of light in a scattering medium upon incidence of modulated light (collimated light).
Figure 4:
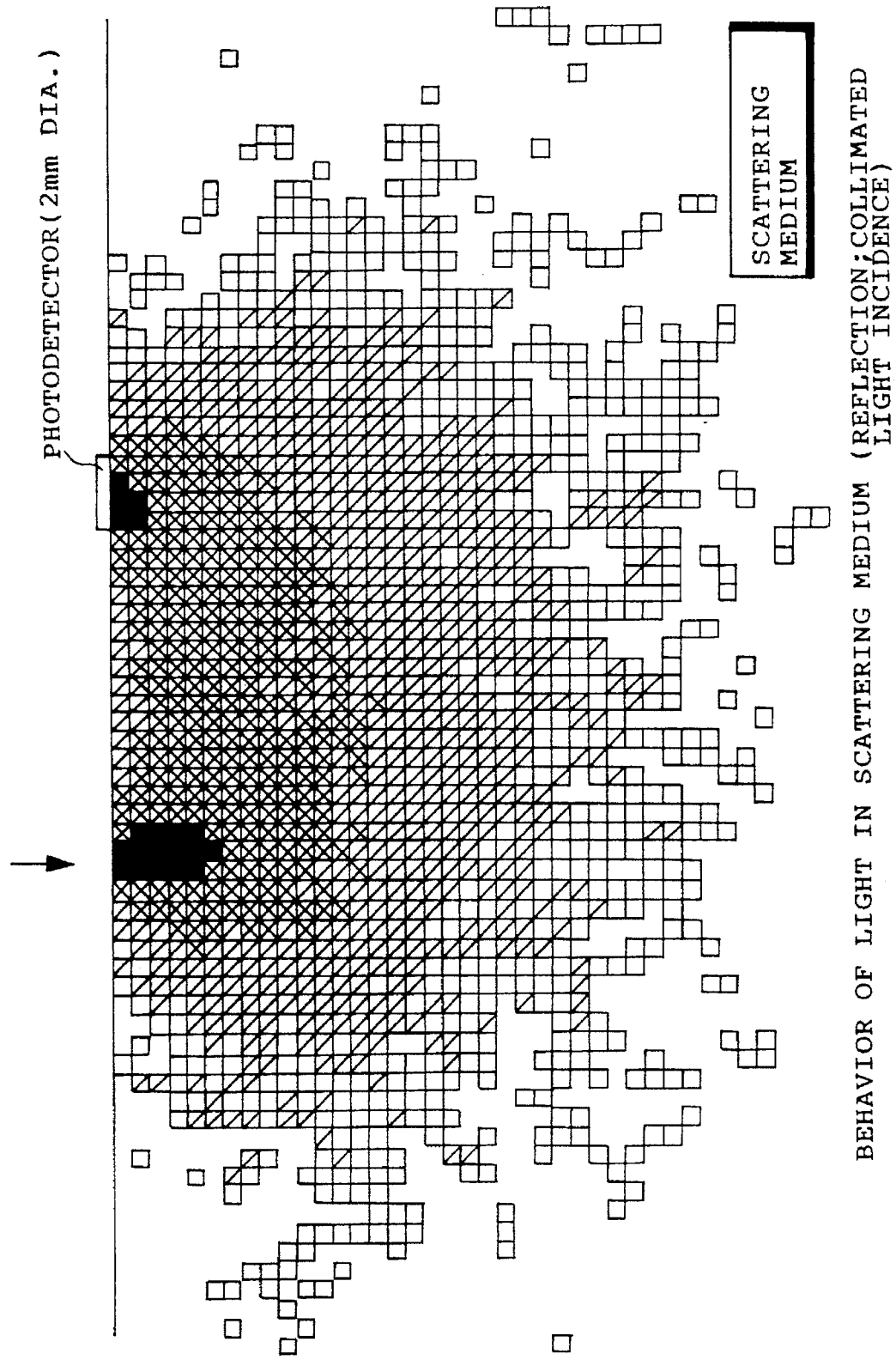
FIG. 4 is a view illustrating the behavior of light (reflection; collimated light incidence) in a scattering medium.
Figure 5:
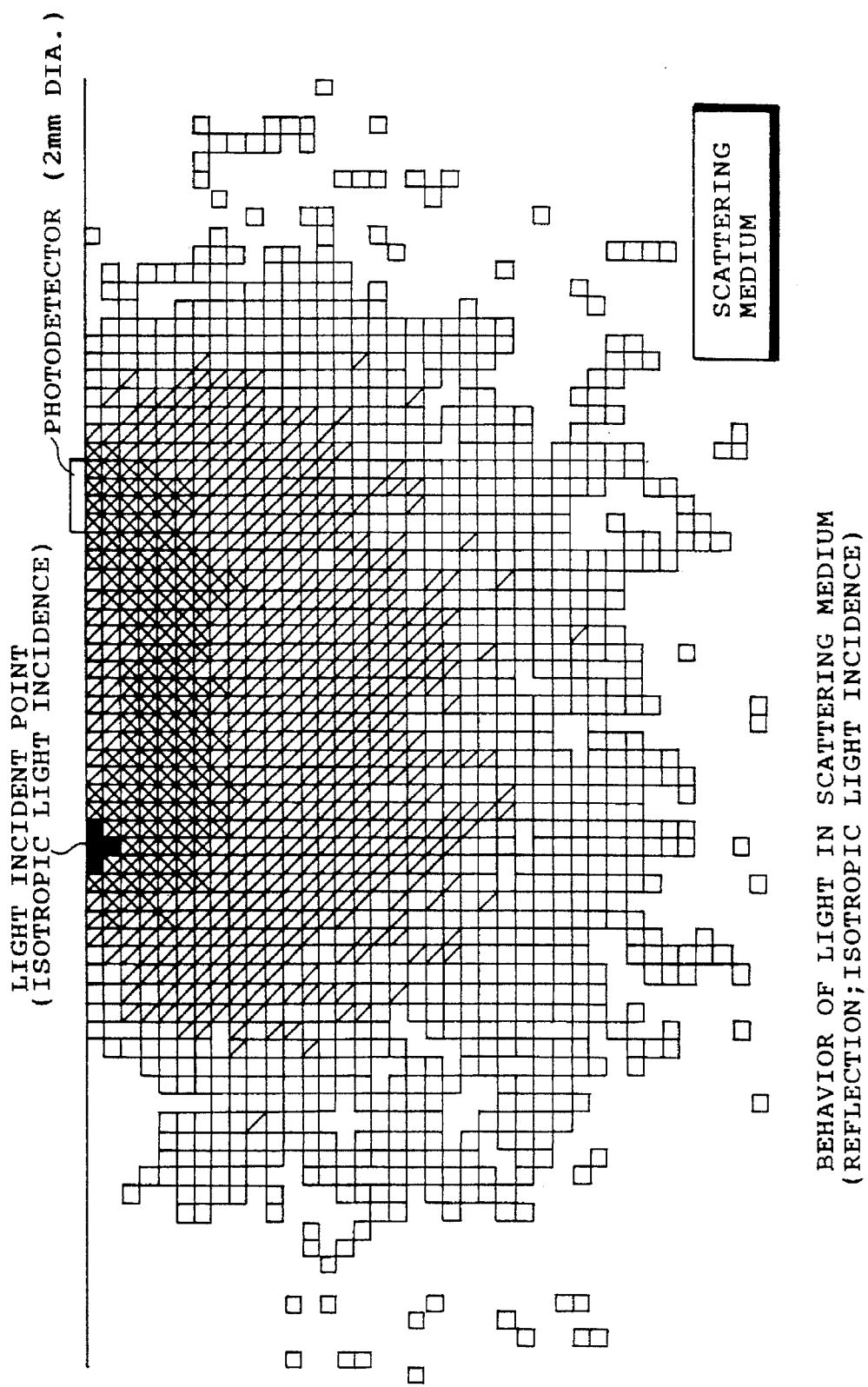
FIG. 5 is a view illustrating the behavior of light (reflection; isotropic light incidence) in a scattering medium.

FIG. 4 and FIG. 5 are results of the simulation of reflection measurement, and show and compare a case in which collimated light is normally incident on a surface of a scattering medium (see FIG. 4) and a case in which light having all incident angle components, that is, isotropic light is incident on a scattering medium (see FIG. 5). In FIG. 4 and FIG. 5, the frequency of a detected photon passing through each position in a scattering medium is shown. Note that the frequency is normalized with frequency at the light incident position. Accordingly, it is known from FIG. 4 and FIG. 5 which position and how frequently a detected photon passes through. Note that in FIG. 4 and FIG. 5 as the mark goes ■, ×, \, □, frequency is decreased by a factor of ten.

In FIG. 4, after incident light travels about 2–3 mm (at ■) in a straight line, light diffusion is started. This is an effect of $z_0{}'$ as described above. In result, in FIG. 4, frequency distribution, that is, optical path distribution, of light diffused during propagation are asymmetric at the light incidence and photodetection side, and the optical path distribution on the light incidence side extends towards the bottom of paper. On the contrary, in FIG. 5, light diffusion is started immediately after light incidence and optical path distributions on the photodetection side and on the light incidence side are substantially symmetrical.

The conditions used in the Monte Carlo calculation are that a distance between a light incident point and a photodetection point (also simply called photodetection length) is 10 mm, and that a diameter of a photodetector is 2 mm, and that a transport scattering coefficient and an absorption coefficient of a scattering medium is 0.45 mm$^{-1}$ and 0.01 mm$^{-1}$, respectively If a plurality of light incident pants are made to be incident on a region having a predetermined area, and a diameter of the light incident position and a diameter of the photodetector are made equal, a symmetrical property of the optical path distribution is further improved.

Figure 6:
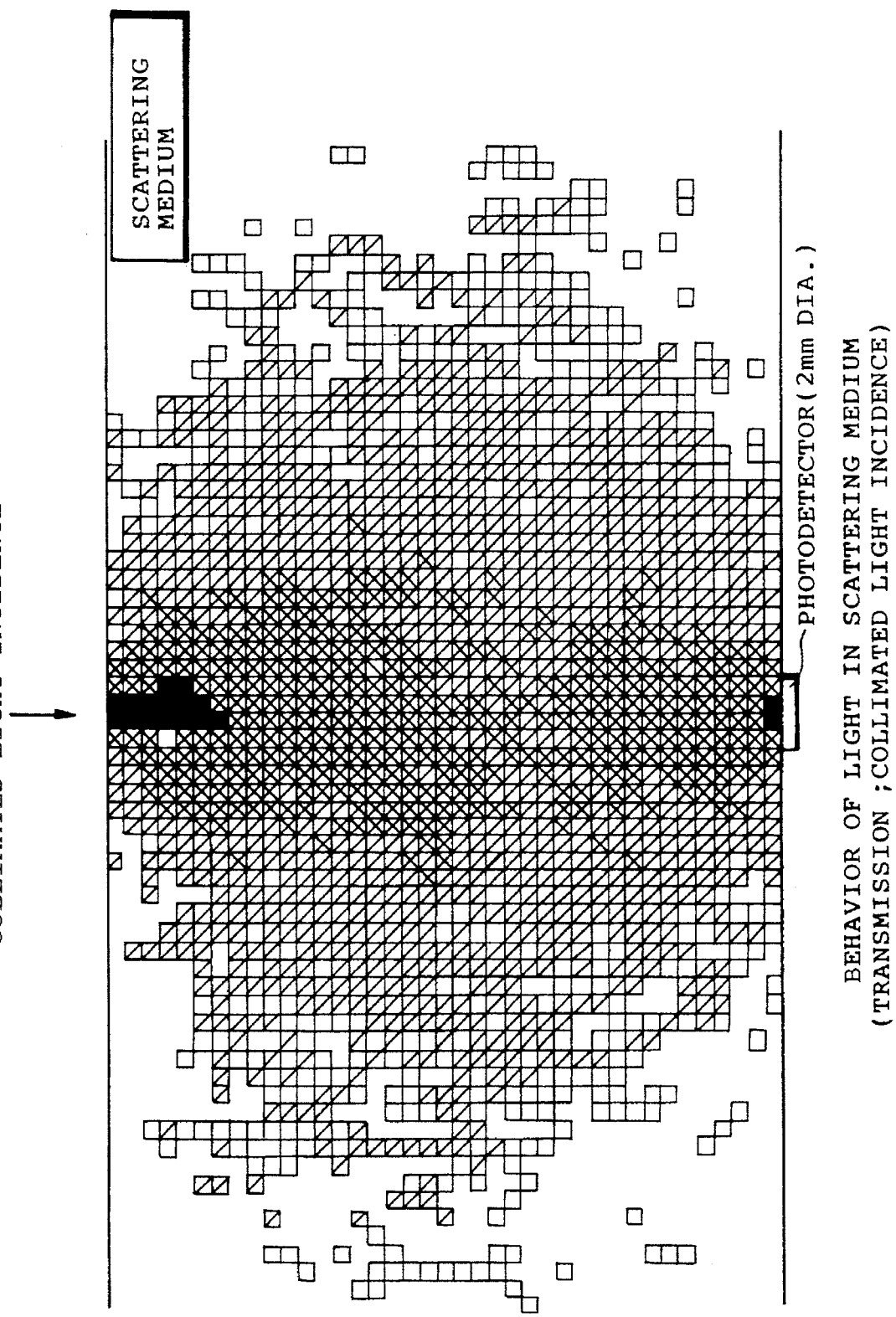
FIG. 6 is a view illustrating the behavior of light (transmission; collimated light incidence) in a scattering medium.
Figure 7:
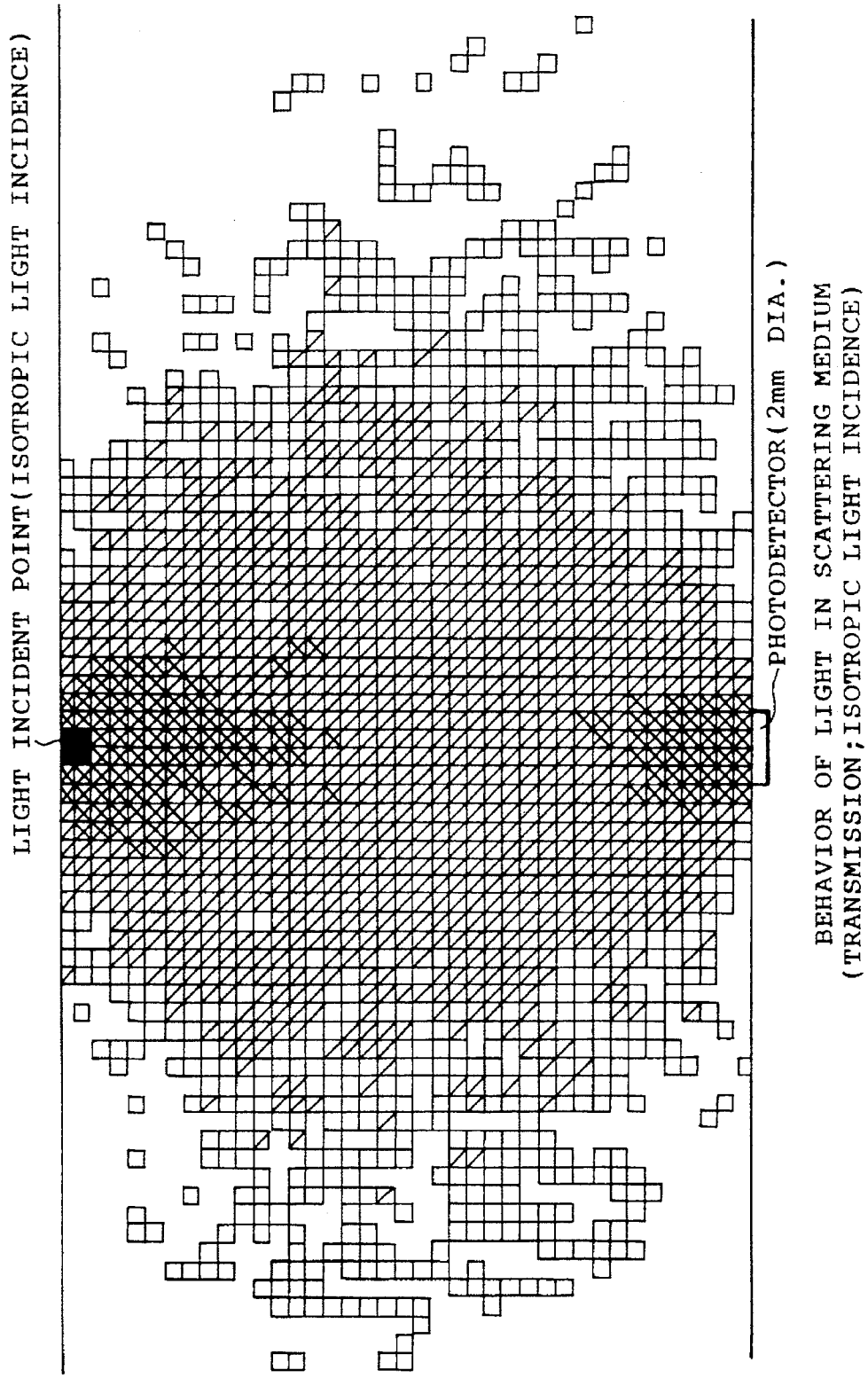
FIG. 7 is a view illustrating the behavior of light (transmission; isotropic light incidence) in a scattering medium.

FIG. 6 and FIG. 7 show simulation results of transmission measurement, and show and compare the situation where collimated light is normally incident on a surface of a scattering medium (see FIG. 6) and the situation where light having all incident angle components, that is, isotropic light, is incident on a scattering medium (see FIG. 7). The symbols used in FIG. 6 and FIG. 7 are the same as those used in FIG. 4 and FIG. 5. in FIG. 6, the effects of $z_0{}'$ clearly appear. In FIG. 7, as similar to the reflection measurement, the optical path distributions on the light incident side and the photodetection side are substantially symmetric.

The conditions used in the Monte Carlo calculation are that a distance between a light incident point and a photodetection point, that is, a thickness of the scattering medium, is 20 mm, and that a diameter of a photodetector is 2 mm, and that a transport scattering coefficient and an absorption coefficient of a scattering medium is 0.45 mm$^{-1}$ and 0.01 mm$^{-1}$, respectively. Similar to the reflection measurement, if the diameter of the light incident position and the diameter of the photodetector are made equal, the symmetric property of the optical path distribution is further improved.

The following new important information to be utilized in the invention of the present application can be attained. In other words, when light having various incident angle components is incident on the scattering medium, it can be considered that an equivalent point light source or a group of equivalent point light sources are generated near or on a surface of the scattering medium and light diffusion starts from a position of the equivalent light source. Further, in the case of the scattering medium having a different scattering coefficient, the equivalent light source is generated near or on the surface of the scattering medium, so that in the case of the different kinds of scattering media, a position at which light diffusion starts is the same, that is, light incident conditions are the same. Accordingly, treatment of light traveling straight after light incidence which is one of problems in the conventional techniques becomes very easy and there is no need to use approximation or assumption for a traveling distance in a straight line, so that the measurement accuracy of measurement of internal information in the scattering medium can significantly be improved.

The frequency distributions, that is, the optical path distributions, on the light incident side and the photodetection side are symmetric, which means that the reciprocity theorem (also called reversible theorem) holds. This case implies that even if the light incident position and the photodetection point are switched, the optical path distributions are unchanged. Accordingly, with use of such a symmetric property, the measurement accuracy of measurement of internal information in the scattering medium can significantly be improved. It is apparent that the above information has great effects in the case of measurement of position of a specific absorptive constituent and in the case of restructuring of cross sectional image of inside of the scattering medium.

Note that in the above, the case of incidence of light having all incident angle components on the scattering medium has been described, but the actual incident light may have only incident angle components corresponding to the scattering medium, e.g., semi-infinite space. Further, as the limitation of incident angle distribution is examined, when the angle of incidence uniformly distributes within a range of 0° to about 30°, almost all of the above description holds. Accordingly, when a simple optical system is used in an actual apparatus, pay attention to the above-described incident angle distribution.

2. Introduction of New Mathematical Model

The inventors of the present application theoretically and experimentally examined the light incident conditions, that is, the behavior of light having various incident angle components incident on the scattering medium, and developed a new model including a boundary condition and then obtained the following knowledge. This knowledge is that the results derived from the model with the application of the light diffusion theorem, the results of Monte Carlo calculation and the actual experimental results well match. In the case of the application of the light diffusion theorem, a method for setting a boundary condition and an approximation method when the relation of various parameters are derived from a photon fluence rate $\phi$ needs to be considered sufficiently. When the photon diffusion equation is solved with the application of the boundary condition, errors in the internal information of the scattering medium, which is a final target of measurement, need to be carefully estimated, and the approximation which can ignore the errors needs to be selected and applied.

A relation between a photon diffusion equation and optical constants of a scattering medium and a relation between a mathematical model developed by the inventors of the present application and a boundary condition will be described.

(1) Relation between Photon Diffusion Equation and Optical Constants

First, the photon diffusion equation and various optical constants relative to the scattering medium will be explained. These definitions and symbols are frequently used in next detailed description.

The photon diffusion equation which describes the behavior of light or photons in the scattering medium is derived from the diffusion approximation of the photon transport theorem and for example, may be expressed by following equation using a photon fluence rate $\phi$.

$$(1/c)(\partial \phi(r,t)/\partial t) - D\nabla^2 \phi(r,t) + \mu_a \phi(r,t) = S(r,t) \qquad (1.1)$$

where $\phi$: the photon fluence rate at position r, at time t [photon/mm$^2$·sec]

Note that r is a vector.

D: the diffusion coefficient [mm]

$\mu_a$: the absorption coefficient [mm$^{-1}$]

c: the speed [mm/sec] of light in a scattering medium (given by a refractive index of a scattering medium)

S(r,t): light source [photon/mm$^3$·sec].

Since an impulse light source can be expressed by a delta function, a light impulse incident on an origin (r=0) at t=0 can be expressed by the following equation.

$$S(r,\, t) = \delta(r,\, t) = \delta(0,\, 0) = \delta(0) \cdot \delta(0) \qquad (1.2)$$

Consequently, the photon diffusion equation corresponding to impulsed light incidence is as follows:

$$(1/c)(\partial\phi(r,t)/\partial t) - D\nabla^2\phi(r,t) + \mu_a\phi(r,t) = \delta(0,0) \quad (1.3)$$

where $\delta(0,0)$ is a light impulse incident on an origin ($r=0$) at $t=0$. Details are omitted but the solution of the photon diffusion equation can be obtained using a formula.

Relations between the various optical constants on a scattering medium are, for $\mu_s$: the scattering coefficient [mm$^{-1}$]

$\mu_s'$: the transport scattering coefficient [mm$^{-1}$]

$\mu_{tr}$: the transport attenuation coefficient [mm$^{-1}$]

$\mu_{eff}$: the effective attenuation coefficient [mm$^{-1}$]

g: the mean cosine $\theta$ of the scattering angle $\theta$ $\omega$: the angular frequency of modulated light to be incident on a scattering medium, $$D=[3(\mu_a+\mu_s')]^{-1}=(3\mu_{tr})^{-1} \text{ or } 3(\mu_s')_{-1} \quad (1.4)$$

$$\mu_s'=(1-g)\mu_s \quad (1.5)$$

$$\mu_{tr}=\mu_a+\mu_s'=\mu_a+(1-g)\mu_s \quad (1.6)$$

$$\mu_{eff}=[\mu_a/D]^{1/2} \quad (1.7)$$

Further, parameters derived from the photon fluence rate $\phi$ are

J: photon current or photon current density [photon/mm$^2$·sec]

$<L>$: average optical pathlength=$c<t>$ [mm]

Note that $<t>$ is the mean delay time of temporal waveform of photon current or the mean time of photon flight dJ/dt: time differentiation of photon current I: time integral value of photon current [photon/mm$^2$]

F($\omega$): Fourier spectrum of photon current J $\Phi$: phase delay of F($\omega$) [radian], which are frequently used in next detailed description. Note that temporal waveform of photon current density expresses the distribution of time of flight of photon. Further, a quantity to be determined in the actual measurement is an optically detected signal. The optically detected signal is processed to derive the primary information such as the average optical pathlength, the time integral value, slope (differential value), or the amplitude or phase delay, of signal having a specific frequency component. Note that in the present invention, such primary information is called a predetermined parameter.

There is a concept of partial photon current in the photon transport theory. This is defined by a photon current $J_+$ passing a unit area in the scattering medium from left to right and a photon current $J_-$ passing there from right to left, and the photon current J expressing a real photon current is a difference between the partial photon currents, that is, $$J=J_+-J_- \quad (1.8)$$

Here, as diffusion is approximated, the partial photon current at a position r is expressed by $$J_+(r)=(1/4)\phi(r,t)-(D/2)e_S\cdot\nabla\phi(r,t) \quad (1.9)$$

$$J_-(r)=(1/4)\phi(r,t)+(D/2)e_S\cdot\nabla\phi(r,t) \quad (1.10)$$

Note that $e_S$ is a unit vector in a direction of normal of the unit area. Accordingly, in the diffusion approximation, the equations (1.8) to (1.10) hold everywhere in the scattering medium.

(2) Boundary Condition and Model

Figure 8:
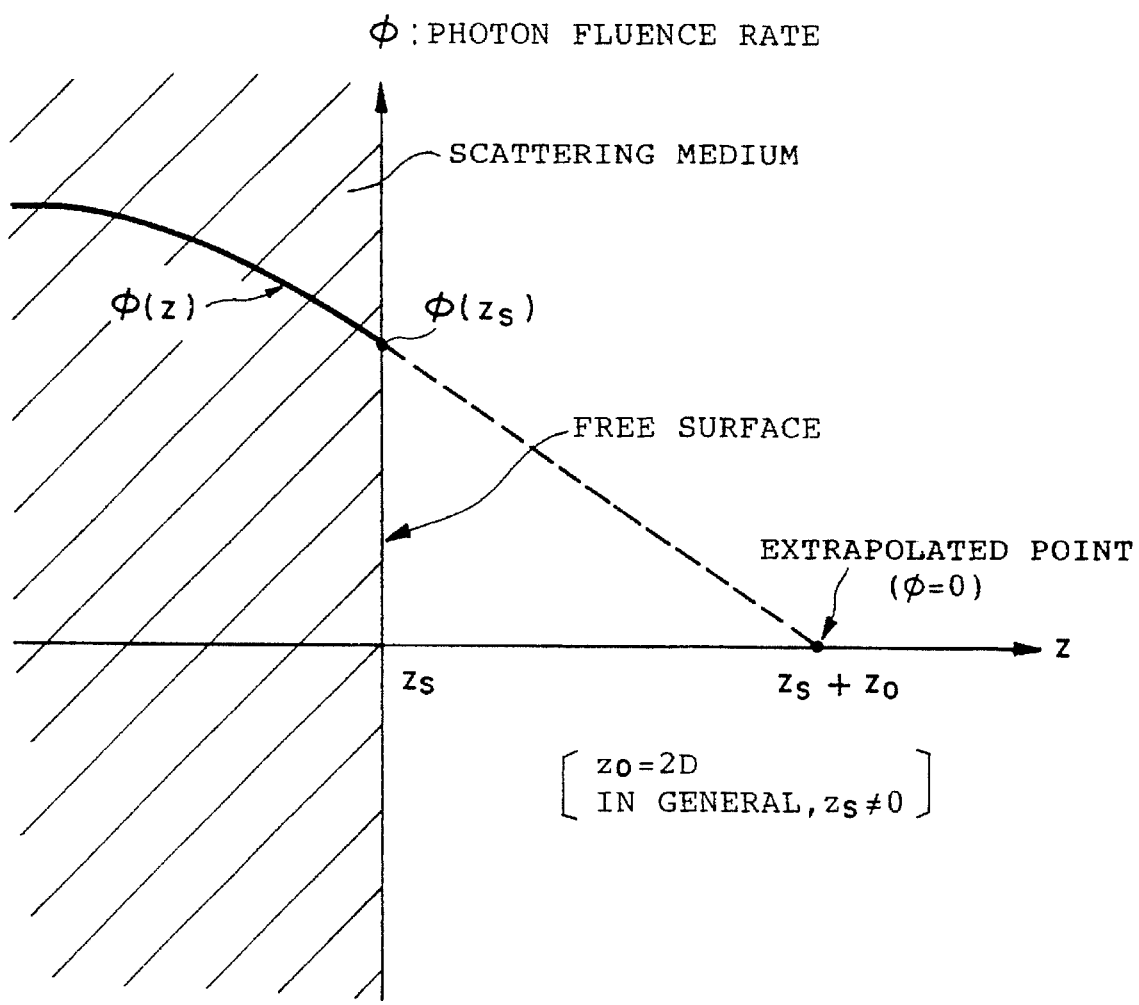
FIG. 8 is a view illustrating a photon fluence rate φ near a free surface.
Figure 9:
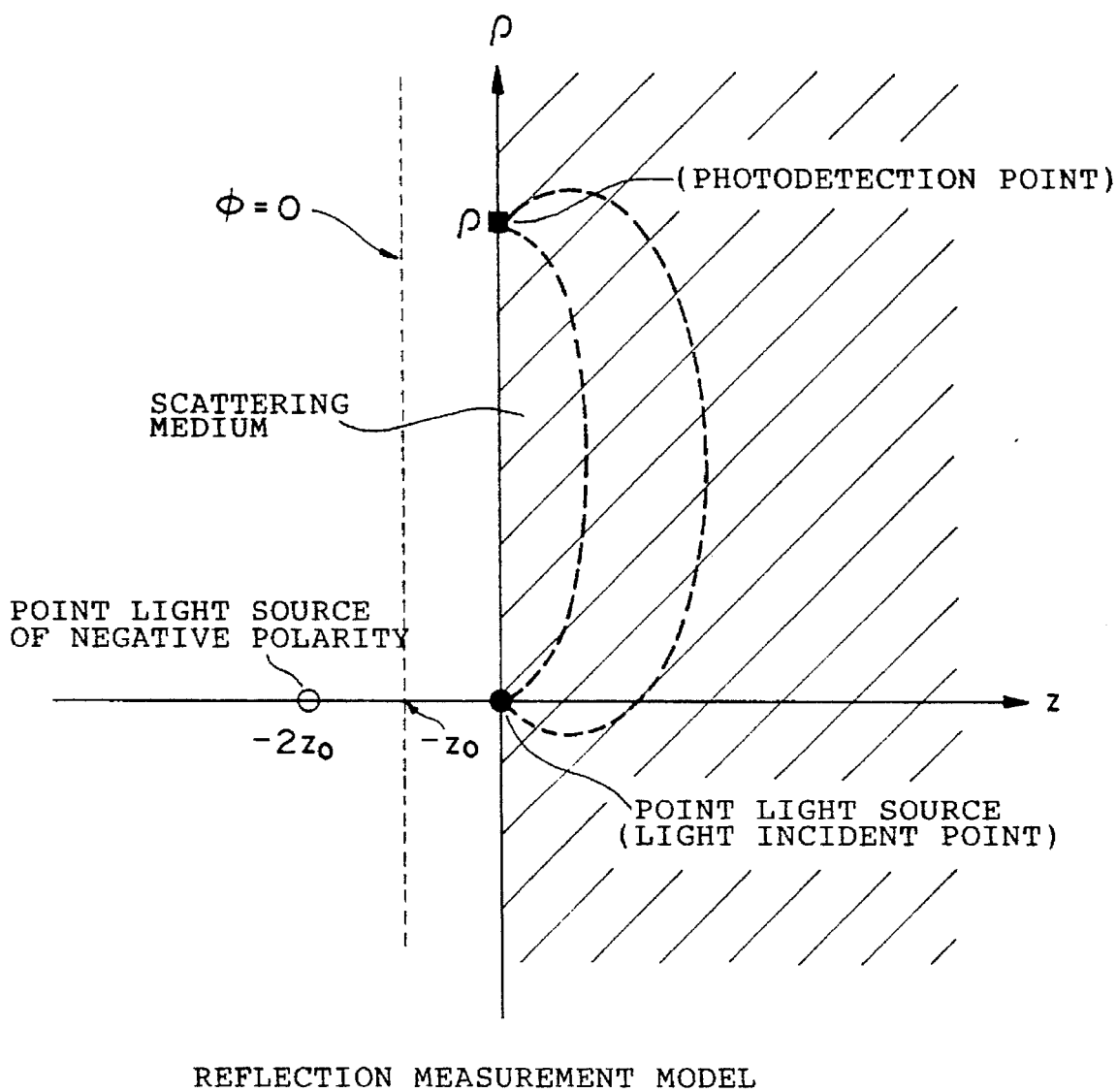
FIG. 9 is a view illustrating a model for reflection measurement.

According to the photon transport theory, the photon fluence rate $\phi$ at the free surface (for convenience' take, $z=z_S$) is a finite value $\phi(z_S)\neq 0$, and as shown in FIG. 8, the photon fluence rate $\phi$ becomes $\phi=0$ at a position separated apart from the free surface by $z_0$. Taking the above description into consideration, the model for reflection measurement and the model for transmission measurement are shown in FIG. 9 and in FIG. 10, respectively. In these models, light is made to be incident on an origin in FIG. 9 and FIG. 10. Further, a point light source of negative polarity is set on a position separated apart from the free surface by $-2z_0$ in order to satisfy the above boundary conditions. In result, the photon fluence rate becomes $\phi(-z_0)=0$ at a position $z=-z_0$. Note that ● and ○ in FIG. 9 and FIG. 10 indicate a point light source of positive polarity and a point light source of negative polarity, respectively.

Figure 10:
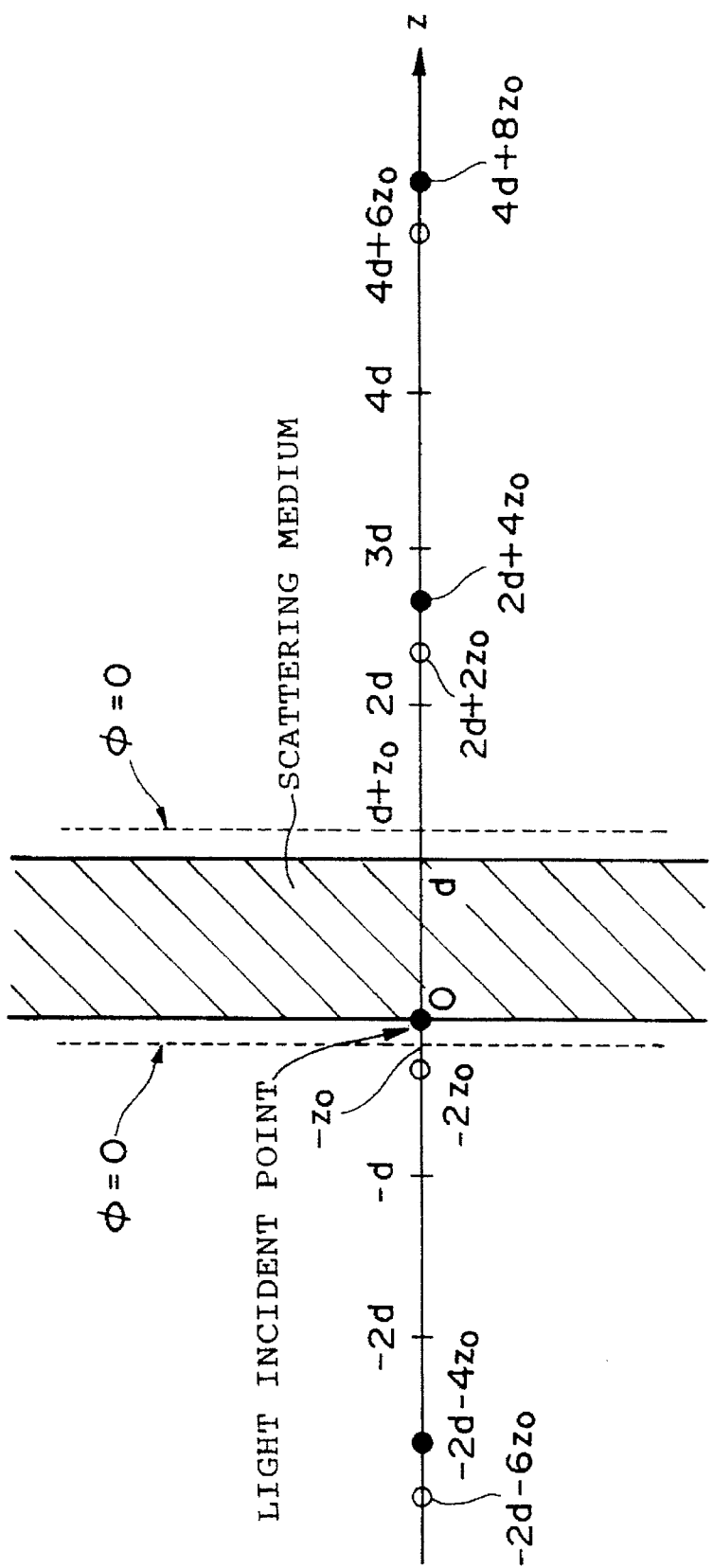
FIG. 10 is a view illustrating a model for transmission measurement.

In FIG. 9 and FIG. 10, light having various incident angle components is incident on the light incident position (the origin) on the surface of the scattering medium. Further, in the transmission model of FIG. 10, an infinite number of point light sources of positive polarity and negative polarity are set in order to satisfy the above boundary conditions on both the light incident and the photodetection sides. Note that in practice, approximation can be performed with sufficient accuracy with a finite number of point light sources of positive polarity and negative polarity.

Further, in the photon diffusion theory, $z_0$ is $$z_0=2D \quad (2.1)$$

but in the strict photon transport theory, $$z_0=0.7104/\mu_{tr}=2.1312D \quad (2.2)$$

Here, the photon fluence rate $\phi$ derived by diffusion approximation can be obtained with high accuracy at locations sufficiently separated apart from the light source in the scattering medium and the free surface. However, considering a fact that near the free surface, the photon fluence rate $\phi$ is a quite precise value but in principle, only the approximated value is obtained, $z_0$ will not differ largely for either of equations (2.1) and (2.2). Therefore, the boundary condition and the model will be explained based on the equation (2.1), that is, $z_0=2D$.

Note that, in the usual measurement system, light is incident on a scattering medium from air, and light is detected in air. In this case, $z_0$ is a function of refractive index of air and refractive index of scattering medium (this is described, e.g., in the reference 6)). However, since the refractive index of the scattering medium can be considered to be equal to that of water, both refractive indices are considered to be constant, and then the equation expressing a relation between $z_0$ and D is the equation (2.1) in which the proportional constant is varied. However, in such a case, it can also be proved that a fact, which will be described next, holds. Further, for the measurement requiring the high accuracy which is unable to neglect the above approximation, the obtained photon fluence rate $\phi$ needs to be compensated, which will be described later.

Next, the specific boundary condition to be applied to the photon diffusion equation will be obtained. For example, the boundary condition is that photon current $J_-$ (photon/mm$^2$·sec) flowing from outside becomes $J_-=0$ at the surface of the scattering medium, that is, the free surface $r_S$.

From the equation (1.10), the boundary condition becomes $$J_-(r_S)=(1/4)\phi(r_S,t)+(D/2)e_S\cdot\nabla\phi(r_S,t)=0 \quad (2.3)$$

where $e_S$ is a unit vector in a direction of normal of the free surface. In one dimension problem, this equation becomes $$J_-(z_S)=\tfrac{1}{4}\phi(z_S,t)+D/2\cdot(\partial\phi/\partial z)|_{z_S}=0 \quad (2.4)$$

where $(d\phi/dz)|z_S$ is a value of $d\phi/dz$ (differentiation) at $z=z_S$, that is, free surface $z_S$. Further, if the above-described Fick's law is applied to the boundary condition, the equation (2.1) is derived.

On the other hand, from the equation (1.9), photon current $J_+$ flowing from the free surface $z_S$ is $$J_+(z_S)=1/4\phi(z_S,t)-D/2\cdot(\partial\phi/\partial z)|_{z_S} \quad (2.5)$$

where $J=J_+-J_-$. Accordingly, photon current flowing from the free surface, that is, photon current J to be detected can be described by the following two ways.

$$J_g=-D\cdot(\partial\phi/\partial z)|_{z_S} \quad (2.6)$$

or $$J_\phi=\phi(z_S,t)/2 \quad (2.7)$$

where subscripts g and $\phi$ denote a gradient of photon fluence rate $\phi$ and photon fluence rate $\phi$, that is, a kind of parameters used to derive J. If $z_0$32 2D can be considered to be sufficiently small compared to a distance $\rho$ or d between the light incident position and the photodetection point, it can be proved that both equations (2.6) and (2.7) are equivalent.

In the present invention, the predetermined parameters expressed by the above two ways, that is, the average optical pathlength <L>, time differential value of photon current, time integral value I of photon current, Fourier transform F($\omega$) of photon current and its phase delay $\Phi$ etc. (primary information) are obtained, and internal information in the scattering medium, which is secondary information, is determined from the primary information by arithmetic operation. Note that if $z_0=2D$ can be considered to be sufficiently small compared to a distance $\rho$ or d between the light incident position and the photodetection point, it can be proved that the predetermined parameters expressed by the above two ways are equivalent in both cases.

3. Solution of Photon Diffusion Equation and Various Parameters Derived therefrom Next, the solution of the photon diffusion equation, that is, the photon fluence rate $\phi$ is obtained from the mathematical model, and an equation relative to the various predetermined parameters is derived from the photon fluence rate $\phi$. If the approximation is applied during derivation process, it needs to be confirmed that errors in the value of internal information in the scattering medium which is an object of the measurement is able to be neglected. Note that the solution of the photon diffusion equation and the equation relative to the various parameters derived therefrom, which will be described later, are one of the examples. It is apparent that a solution in a different form and an equation in a different form, which is derived therefrom can be used in the present invention.

First, the solution of the photon diffusion equation for the semi-infinite medium shown in FIG. 9 becomes $$\phi(\rho,z,t) = c(4\pi cDt)^{-3/2} \exp(-c\mu_a t) \times \quad (3.1)$$
$$\{\exp[-(z^2 + \rho^2)/(4cDt)] - \exp[-((z + 2z_0)^2 + \rho^2)/(4cDt)]\}.$$

The photon fluence rate $\phi$ is a solution of the photon diffusion equation under the boundary condition shown in FIG. 9, and the predetermined parameters, that is, the photon current density J, average optical pathlength <L>, time integral value i of photon current density, Fourier transform F($\omega$) of photon current density, phase delay $\Phi$ etc. can be derived from the photon fluence rate $\phi$.

One significant point is that the photon current density J, average optical pathlength <L>, time integral value I of photon current density, Fourier transform F($\omega$) of photon current density, phase delay $\Phi$ etc. become a function of two unknown values: the absorption coefficient $\mu_a$ and the transport scattering coefficient $\mu_s'$, and a plurality of known values. Note that the known values are the speed c of light, wavelength $\lambda$ of incident light, distance $\rho$ between the light incident position and the photodetection point, angular frequency $\omega$ of a modulated component of modulated light etc.

Accordingly, variable or controllable known values, for example, in the above example, the distance $\rho$ between the light incident position and the photodetection point or the angular frequency of the modulated light are set to two or more values and the scattering medium is measured. The obtained optically detected signal, that is, the measured value is processed to detect one of the parameters, and based on the two or more simultaneous equations corresponding to the parameter, two unknown values, that is the absorption coefficient $\mu_a$ and the transport scattering coefficient $\mu_s'$ are able to be obtained by arithmetic operation. In this case, of course, as the number of independent measured values is large, the accuracy of the arithmetic operation is improved.

The following parameters are examples of the predetermined parameters, and these parameters are all derived from the equation (3.1). Further, it has been confirmed that next equation expressing the predetermined parameter well matches with Monte Carlo calculation by the inventors of the present invention or the experimental results.

Considering $z=0$ at a photodetection point in the reflection measurement, the photon current J is $$J_g=(4\pi cD)^{-3/2}z_0 t^{-5/2}\exp\{-q^2/(4cDt)-c\mu_a t\} \quad (3.2)$$

$$J_\phi=(1/2)c(4\pi cDt)^{-3/2}\exp(-c\mu_a t) \times\{\exp(-\rho^2/(4cDt)-\exp(-q^2/(4cDt))\}$$

The average optical pathlength <L> is $$<L> = c\left[\int_0^\infty tJ(\rho,t)dt\right]/\left(\int_0^\infty J(\rho,t)dt\right) \quad (3.4)$$
$$= [1/(2D)] \cdot [q^2/(1+q\mu_{eff})].$$

Further, the time integral value I of the photon current density J is $$I_g=[1/(2\pi)]\cdot(z_0/q^3)(q\mu_{eff}+1)\exp(-q\mu_{eff}) \quad (3.5)$$

$$I_\phi=[1/(4\pi z_0)]\{(1/\rho)\exp(-\rho\mu_{eff})-(1/q)\exp(-q\mu_{eff})\} \quad (3.6)$$

Furthermore, the phase delay $\Phi$ of the Fourier transform F($\omega$) of the photon current density J is $$\Phi_g(\omega) = (q\mu_{eff}/\sqrt{2})[(1+\tan^2\Theta)^{1/2}-1]^{1/2}- \quad (3.7)$$

-continued $$\Phi_\psi(\omega) = (\rho\mu_{eff}/\sqrt{2})[(1+\tan^2\Theta)^{1/2}-1]^{1/2} - \tan^{-1}\{\rho\mu_{eff}\tan(\Theta/2)/(\rho\mu_{eff}+[1-\tan^2(\Theta/2)]^{1/2})\} \quad (3.8)$$

where $$z_0 = 2D \quad (3.9)$$

$$q^2 = \rho^2 + (2z_0)^2 \quad (3.10)$$

$$\Theta = \tan^{-1}(\omega/c\mu_a) \quad (3.11)$$

Further, the second term in the equations (3.7) and (3.8) is $-\Theta/2$ for $q\mu_{eff} \gg 1$ or $\rho\mu_{eff} \gg 1$ and $\Phi < 1.5$ [radian].

Next, the transmission measurement will be explained. The solution of the photon diffusion equation for the slab model shown in FIG. 10 is given by $$\phi(\rho,z,t) = c(4\pi cDt)^{-3/2}\exp(-\rho^2/(4cDt) - c\mu_a t) \times \quad (3.12)$$
$$\{\exp(-z^2/(4cDt)) - \exp(-(z+2z_0)^2/(4cDt)) +$$
$$\exp(-(z-2d-4z_0)^2/(4cDt)) - \exp(-(z-2d-2z_0)^2/(4cDt)) +$$
$$\exp(-(z+2d+4z_0)^2/(4cDt)) - \exp(-(z+2d+6z_0)^2/(4cDt)) +$$
$$\exp(-(z-4d-8z_0)^2/(4cDt)) - \exp(-(z-4d-6z_0)^2/(4cDt)) +$$
$$\ldots\}.$$

In the same way as the reflection measurement, various predetermined parameters, for example, the photon current density J, the average optical pathlength <L>, the time integral value I of the photon current density, the Fourier transfer $F(\omega)$ of the photon current density, the phase delay $\Phi$ etc. can be derived from the solution, that is, the photon fluence rate $\phi$.

The significant point is that similar to the reflection measurement; the obtained predetermined parameters, that is, the photon current density J, the average optical pathlength <L>, the time differentiation dJ/dt of the photon current J, the time integral value I of the photon current density J, the Fourier transform $F(\omega)$ of the photon current density J and its phase delay $\Phi$ etc. can be expressed by the two unknown values: the absorption coefficient $\mu_a$ and the transport scattering coefficient $\mu_s'$ and a plurality of known values. Note that the above known values are speed c of light in the scattering medium, wavelength $\lambda$ of the incident light, distance $\rho$ between the light incident position and the photodetection point, angular frequency $\omega$ of the modulated component of the modulated light and others.

Accordingly, variable or controllable known values, for example, in the above example, the distance $\rho$ between the light incident position and the photodetection point or the angular frequency of the modulated light are set to two or more values and the scattering medium is measured. The obtained optically detected signal, that is, the measured value is processed to detect one of the parameters, and based on the two or more simultaneous equations corresponding to the parameter, two unknown values, that is the absorption coefficient $\mu_a$ and the transport scattering coefficient $\mu_s'$ are able to be obtained by arithmetic operation. In this case, of course, as the number of independent measured values is large, the accuracy of the arithmetic operation is improved.

The following parameters are examples of the predetermined parameters, and these parameters are all derived from the equation (3.12). Further, it has been confirmed that next equation expressing the predetermined parameter matches well with Monte Carlo calculations by the inventors of the present invention or the experimental results. Note that the model constituted with an infinite number of the point light sources of positive and negative polarities can be approximated by two point light sources of positive polarity and two point light sources of negative polarity, so that the parameters will be explained with this approximation below. Here, one should note that the following parameters are obtained by a method similar to the following, using more positive and negative point light sources.

Considering a fact that $\rho=0$ at a photodetection point in the transmission measurement, the two kinds of photon currents J are $$J_g = (1/2)(4\pi cD)^{-3/2}t^{-5/2}\exp\{-c\mu_a t\} \times \quad (3.13)$$
$$\{d\exp[-d^2/(4cDt)] - (d+4z_0)\exp(-(d+4z_0)^2/(4cDt))\}$$

$$J_\phi = (1/2)c(4\pi cDt)^{-3/2}\exp\{-c\mu_a t\} \times \quad (3.14)$$
$$\{\exp[-d^2/(4cDt)] - 2\exp(-(d+2z_0)^2/(4cDt)) +$$
$$\exp(-(d+4z_0)^2/(4cDt))\}.$$

The average optical pathlength <L> is $$<L> = [1/(2D)] \cdot [d^2/(1+d\mu_{eff})] \quad (3.15)$$

for $4z_0 \ll d$.

Further, the time integral value I of the photon current density J is $$I_g = [1/(4\pi d^2)]\exp(-d\mu_{eff}) \times \{(d\mu_{eff}+1) - \quad (3.16)$$
$$[((d+4z_0)\mu_{eff}+1)/(1+(4z_0/d))^2] \cdot \exp(-4z_0\mu_{eff}).$$

$$I_\phi = [1/(4\pi z_0)] \cdot \{(1/d)\exp(-d\mu_{eff}) - \quad (3.17)$$
$$[2/(d+2z_0)]\exp(-(d+2z_0)\mu_{eff}) +$$
$$[1/(d+4z_0)]\exp(-(d+4z_0)\mu_{eff})\}$$

Furthermore, the phase delay $\Phi$ of the Fourier transform $F(\omega)$ of the photon current density is given by $$\Phi_g(\omega) = (q\mu_{eff}/\sqrt{2})[(1+\tan^2\Theta)^{1/2}-1]^{1/2} + \alpha_3 \quad (3.18)$$

$$\Phi_\psi(\omega) = (\rho\mu_{eff}/\sqrt{2})[(1+\tan^2\Theta)^{1/2}-1]^{1/2} + \alpha_4 \quad (3.19)$$

where $\alpha_3$ is $$\tan\alpha_3 = -(\tan(\Theta/2))(1+[1(4z_0/d)-(32z_0^2/d^2)+ \quad (3.20)$$
$$(4z_0/dx)])\exp(-x)/\{1+(z_0/dx^2)\cdot\exp(x) +$$
$$(z_0/dx)[2-(1/x)+(16z_0/d)+(8z_0/dx)]\exp(-x)).$$

For $2z_0\tan(\Theta/2) < 1/4$, and $z_0 \ll d$, $$\alpha_3 = -\tan^{-1}\{(1+\exp(-2z_0\mu_{eff}))\tan(\Theta/2)\} \quad (3.21)$$

$\alpha_4$ is $$\tan\alpha_4 = -x\Theta[(1-(2z_0/d))\exp(x)-(1-(4z_0/d))]/[\exp(x)- \quad (3.22)$$
$$(1-(2z_0/d))]^2$$

For $2z_0\tan(\Theta/2) < 1/4$ and $z_0 \ll d$, $$\alpha_4 = -\tan^{-1}\{(\Theta/2)(4z_0\mu_{eff}/(\exp(2z_0\mu_{eff})-1))\} \quad (3.23)$$

Note that $$x = 2^{1/2}z_0\mu_{eff}((1+\tan^2\Theta)^{1/2}+1)^{1/2} \quad (3.24)$$

In the above case, similar to the reflection measurement, $z_0 = 2D$ and $\Theta = \tan^{-1}(\omega/c\mu_a)$. Further, for $\Theta \ll 1$ and $z_0 \ll d$, the relation $\alpha_3 = \alpha_4 = -\Theta$ is obtained.

4. Measurement of Internal Information

The signal directly obtained by the photodetecting means is equivalent to the photon current density J. Accordingly, in the measurement of internal information in the scattering medium, the optically detected signal is processed to extract the predetermined parameters which are the primary information. Next based on the relations between these predetermined parameters and the scattering characteristic and the absorption characteristic in the diffusion-propagation path of the scattering medium, the internal information in the scattering medium, which is the secondary information, is obtained by the arithmetic process. If the simultaneous equations are needed for this relation upon the arithmetic process, variable or controllable known values, for example, the photodetection distance, the angular frequency of the modulated light etc. are set to two or more values and the scattering medium is measured under these conditions.

For such measurement, absolute value measurement and relative value measurement can be possible. Light having two or more different wavelengths is utilized to measure and determine a specific absorptive constituent and a specific scattering constituent. Considering the internal information obtained above is a line integral value along the diffusion-propagation path corresponding to the light incident position and the photodetection point, cross sectional images as often seen in x-ray CT can be reconstructed, utilizing data obtained by the measurement along the cross section of the scattering medium in various directions.

Some the measurements will be explained blow. Note that it is easily considered that the method and apparatus which will be explained below and modification of these can be utilized for another kind of measurement.

(1) Measurement of Absolute Value of Internal Information

The method for measuring an absolute value of the internal information in the scattering medium can be broadly classified into a method utilizing the predetermined parameters obtained above, that is, the photon current density Jr the average optical pathlength <L>, the time differentiation dJ/dt of the photon current density J, the time integral value I of the photon current density J, the Fourier transform $F(\omega)$ of the photon current density J etc. (hereinafter called light intensity method), and a method utilizing the phase delay $\Phi$ of the Fourier transform $F(\omega)$ of the photon current density J or others (hereinafter called modulated light method). in other words, the former is a method utilizing the relations expressed by the equations (3.2) to (3.6) and equations (3.13) to (3.17). The latter is a method utilizing the relations expressed by the equation (3.7) or (3.8) and the equation (3.18) or (3.19). As one example of the former light intensity method, a method utilizing the relation expressed by the equation (3.5) will be explained below. Note that it is apparent that the method which will be explained below can be applied to light intensity methods in a similar fashion.

Figure 11:
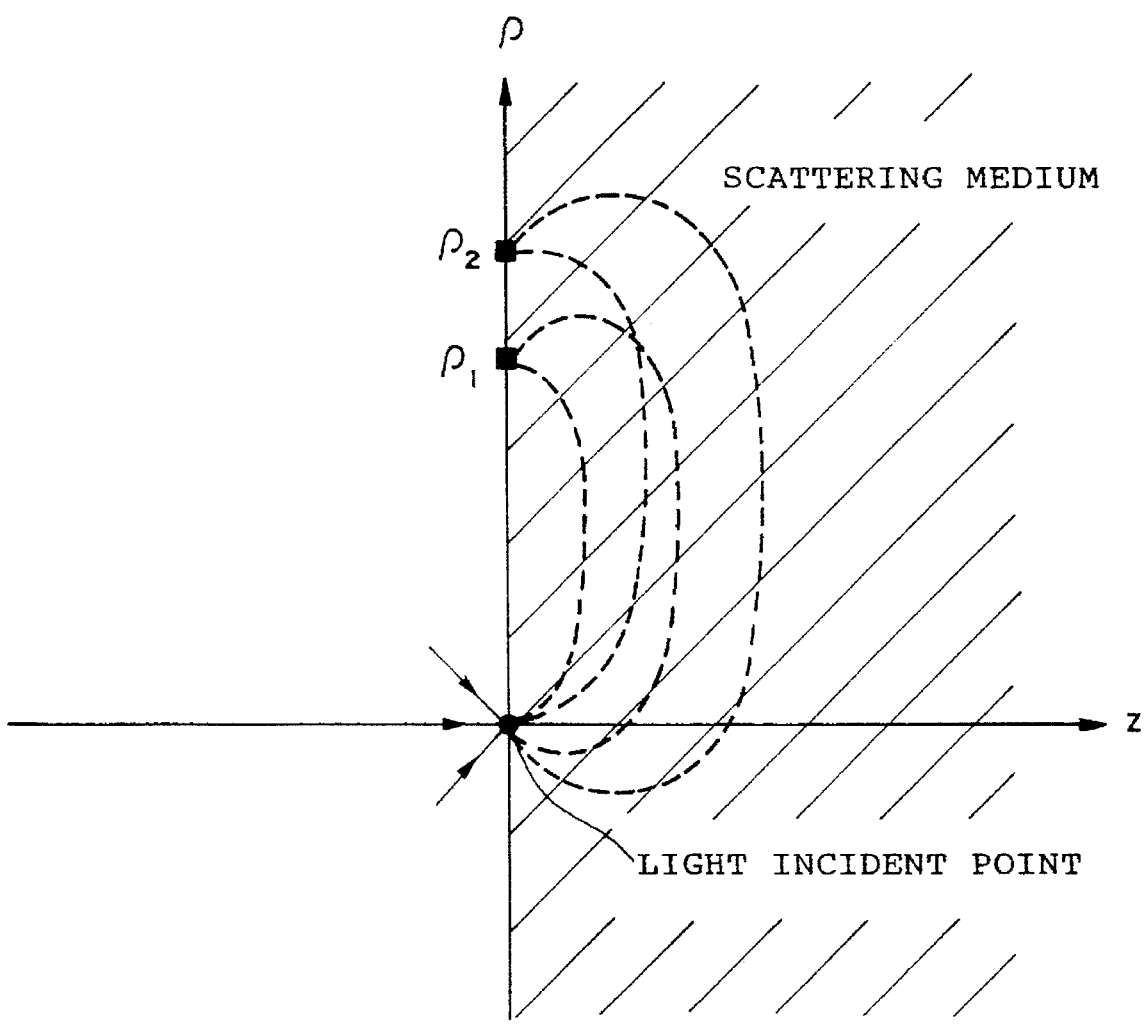
FIG. 11 is a view illustrating the measurement of an absolute value of internal information (reflection measurement).

As shown in FIG. 11, the predetermined parameter $I_g$ shown in the equation (3.5) is assumed to be measured at two different photodetection distances, and the photodetection distances are expressed by $\rho_1$ and $\rho_2$ and two kinds of the measurement values at the detection distances $\rho_1$ and $\rho_2$ are assumed to be expressed as $I[\rho_1]$: the measurement value at the detection distance $\rho_1$ $I[\rho_2]$: the measurement value at the detection distance $\rho_z$ It should be noted that in FIG. 11, one light incident position and two photodetection points are set but it is apparent that if two light incident positions and one photodetection point are used, the same measurement can be performed. Further, this measurement utilizes the integral value of the optically detected signal, so that incident light may have any waveform as long as the integration time can be specified. For example, it is apparent that square waveform light or continuous light can be used.

Two measurement values corresponding to two photodetection distances $\rho_1$ and $\rho_2$ satisfy the next two simultaneous equations which are derived from the equation (3.5).

$$\begin{cases} \ln I(\rho_1) = \ln(z_0/2\pi) - 3\ln q_1 + \ln(q_1\mu_{\text{eff}} + 1) - q_1\mu_{\text{eff}} \\ \ln I(\rho_2) = \ln(z_0/2\pi) - 3\ln q_2 + \ln(q_2\mu_{\text{eff}} + 1) - q_2\mu_{\text{eff}} \end{cases} \quad (4.1)$$

where $q_1{}^2 = \rho_1{}^2 + (2z_0)^2$ $q_2{}^2 = \rho_2{}^2 + (2z_0)^2$ $z_0 = 2D = 2/(3(\mu_a + \mu_s'))$ or $2/(3\mu_s')$ $\mu_{\text{eff}} = (\mu_a/D)^{1/2}$ Two equations forming the simultaneous equations (4.1) are independent from each other and the number of unknown values is two: $\mu_a$ and $\mu_s'$. Accordingly, the two unknown values $\mu_a$ and $\mu_s'$ can be obtained using the two measurement values $I[\rho_1]$ and $I[\rho_2]$, and the values $\rho_1$ and $\rho_2$ which are known values or measured by another method. Further, $\mu_{\text{eff}}$ and $z_0$ can be calculated from values $\mu_a$ and $\mu_s'$.

As described above, to obtain ($\mu_a$ and $\mu_s'$) or $\mu_{\text{eff}}$, the simultaneous equations may be of any form as long as the equations are independent from each other and derived from equation (3.1). The computation to solve such simultaneous equations can be performed at high speed using a computer. Note that the computation accuracy is improved as the number of independent measurement values is large.

The case that the object to be measured is a semi-infinite scattering medium has been explained; however, in practice, a finite scattering medium is generally measured. In this case, the boundary condition should be satisfied outside of the scattering medium shown in FIG. 11, and the condition of photo diffusion should hold for light which is diffused during propagation in the scattering medium. This condition holds when the scattering medium is considered to be sufficiently large as compared with the photodetection distances $\rho_1$ and $\rho_2$. For example, the region in the dashed lines in FIG. 11 shows a region through which most of light passes. The presence of such a region is apparent from a spindle-shaped beam[3] in the scattering medium reported by Sevick et al. or the results of Monte Carlo calculation (e.g., FIG. 4 and FIG. 5). Further, light having various incident angle components is made to be incident on the point of the scattering medium. However, as already explained above, the region on which light is incident can be a region having a finite area, or light in which the incident angle distribution is limited to some extent can be made to be incident. In other words, the former case can be considered as the group of equivalent light sources. In the latter case, as already explained, if the incident angle is uniformly distributed within a range 0° to 30°, the error caused by the limited incident angle can be neglected. If the incident angle is uniformly distributed within a range 0°–45°, the measurement accuracy is further improved.

If the above measurement is performed corresponding to light having two different wavelengths $\lambda_1$ and $\lambda_2$, the respective absorption coefficients $\mu_{a1}$ and $\mu_{a2}$ and the respective transport scattering coefficients $\mu_{s1}'$ and $\mu_{s2}'$ can be obtained. Accordingly, for example, the degree of oxygen saturation of hemoglobin can be calculated from a value of $\mu_{a1}/\mu_{a2}$[4]. In such dual-wavelength spectroscopy, wavelength dependency of the absorption coefficient of the absorptive constituents contained in the scattering medium is utilized. For example, in the measurement of oxyhemoglobin and reduced hemoglobin, or oxymyoglobin and reduced myoglobin, light having a wavelength in which the absorption coefficient difference between oxidation and deoxidation is large, e.g., light having 700 nm to 1.2 μm wavelength is frequently used. Further, if light having a three or more kinds of wavelengths is utilized, improvement in the measurement accuracy and/or measurement of specimens which have background absorption are possible[4].

When the measurement method and apparatus of the present invention are applied to the dual-wavelength spectroscopy, the absolute values of transport scattering coefficients $\mu_{S1}'$ and $\mu_{S2}'$ with respect to the two wavelengths are obtained, which is a big advantage and which is not achieved in the prior art. Therefore, even though the assumption on the conventional dual-wavelength spectroscopy, that is, the assumption that the difference of the scattering coefficients of the scattering constituents with respect to light having two different wavelengths is extremely small, does not hold, the measurement method and apparatus of the present invention can perform the measurement with high accuracy. As described above, the measurement method and apparatus according to the present invention can largely improve the measurement accuracy and expand the application fields against the conventional dual-wavelength spectroscopy. Note that when the transport scattering coefficients $\mu_s'$ with respect to the two different wavelengths can be considered to be equal, the simpler simultaneous equations or a smaller number of simultaneous equations which are modified from the equation (4.1) can be utilized.

Figure 12:
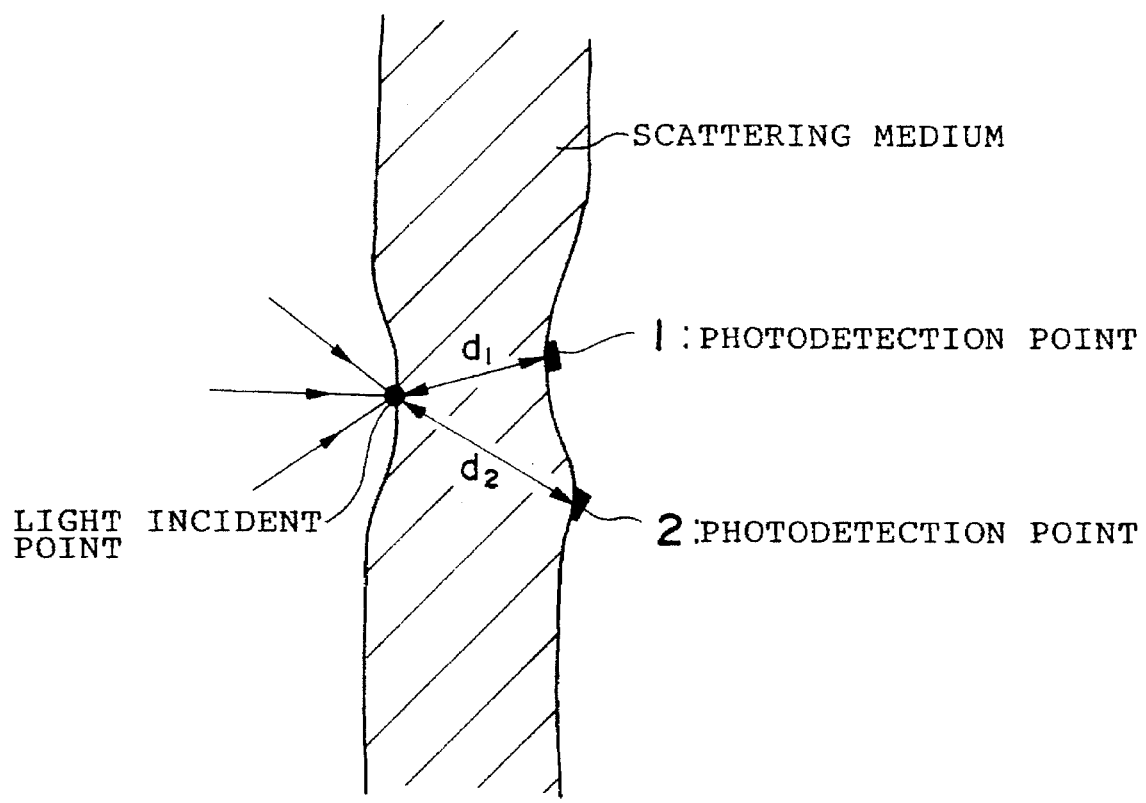
FIG. 12 is a view illustrating the measurement of an absolute value of internal information (transmission measurement).

The measurement method and apparatus which have been described can also be applied to a slab-like specimen, and its state is shown in FIG. 12. Light is incident on one point and diffused light is detected at two points of different photodetection distances in FIG. 12, but if light may be incident on two points and lights are detected at two points of different photodetection distances, the same advantage can be obtained. Note that in such transmission measurement, simultaneous equations derived from the equation (3.12), e.g., equations (3.13) to (3.19) are utilized.

The internal information, i.e., the absorption coefficient $\mu_a$ or the transport scattering coefficient $\mu_s'$ is an integral value or a mean value of information along with the optical path of light which is diffused during propagation to the photodetection point from the light incidence position. Therefore, when change in the internal information is slow as compared with the distance between the light incidence position and the photodetection point shown in FIG. 11, or as compared with the interval of the photodetection points shown in FIG. 12, the spatial distribution of various kinds of the internal information can be imaged, that is, a simple imaging technique by relatively scanning the measurement points, that is, a combination of the light incident position and the photodetection point over the scattering medium. It is apparent that if the above-described measurement is performed at different times, the time change in the internal information can be measured, and it is applied to the measurement or monitoring the amount of oxygen in brain or others. In these cases, the imaging and the computation can be performed at high speed using a computer unit which comprises a memory, a display or others.

If the absorption coefficient $\mu_a$ and the transport scattering coefficient $\mu_s'$ are considered to be line integral values along with the optical path of light which is diffused during propagation corresponding to the light incident position and the photodetection point, cross sectional images as often seen in X-ray CT are able to be reconstructed using these data.

(2) Measurement of Absolute Value Taking Light Attenuation on the Surface into Consideration When light is incident on the scattering medium or when light emerges from the scattering medium, if there is some light attenuation, for example, absorption by a surface colored layer, some error occurs in the absorption coefficient $\mu_a$ or the transport scattering coefficient $\mu_s'$ which is measured based on the measurement principle described in section (1). Further, error caused by the diffusion approximation (which means that in the diffusion approximation, only the approximated value of photon fluence rate $\phi$ is obtained) and the quantum efficiency of the photodetector can be considered together with the light attenuation factor $\eta$.

A measurement method capable of not causing error even though the possibility of error occurrence due to the light attenuation exists will be explained. As one example, a case of utilizing a relation expressed by the equation (3.5) will be explained below; however, when utilizing a relation expressed by an equation in another form derived from the equation (3.1) or (3.12), in the same way, the absolute values of $\mu_a$ and $\mu_s'$ can be measured.

Assuming the attenuation factor $\eta$ of light attenuation is as described above, the photon current density utilized in measurement is derived from the equation (3.2) and given by $$J_{gd} = \eta(4\pi cD)^{-3/2} z_0 t^{-5/2} exp\{-q^2/(4cDt) - c\mu_a t\} \quad (4.2)$$

An equation expressing the photon current utilized in the measurement, that is, the time integral value of the detected signal $J_{gd}$, which means that the equation corresponding to the equation (3.5) is derived from the equation (4.2).

$$I_{gd} = \eta(1/(2\pi))(z_0/q^3)(q\mu_{eff} + 1)exp(-q\mu_{eff}) \quad (4.3)$$

where $q^2 = \rho^2 + (2z_0)^2$.

The unknown values in equation (4.3) are apparently $\mu_a$, $\mu_s'$, and $\eta$. Accordingly, the photodetection distance $\rho$ which is a controllable known value is set to three or more different values, and the above $T_{gd}$ is calculated. Next, based on the simultaneous equations as a function of three or more kinds of $I_{gd}$, the three unknown values, i.e., the light attenuation factor $\eta$, the absorption coefficient $\mu_a$, and the transport scattering coefficient $\mu_s'$ can be calculated. If the above measurement is performed corresponding to light having two different wavelengths, a specific absorptive constituent and a specific scattering constituent can be measured and determined. In this case, the calculation is performed with high speed using a computer. It is apparent that as the number of independent measurement values $I_{gd}$ is large, the calculation accuracy is improved.

The relation between the light incident position and the photodetection point in order to perform such measurement is achieved by obtaining three different photodetection points in FIG. 11 and FIG. 12, for example, by detecting light at three points of different photodetection distances. Alternatively a method for making light to be incident on three points of different photodetection distances and detecting light at one photodetection position can be used. Further, when the attenuation factor $\eta$ is a known value or measured by another method, the method described in section (1) can be utilized.

(3) Measurement of Internal Information by Modulated Light Method

In the absolute value measurement by a modulated light method, the relations between the phase delay $\Phi$, the absorption coefficient $\mu_a$ and the transport scattering coefficient $\mu_s'$ expressed by the equations (3.7) and (3.8) or the equations (3.18) and (3.19), that is, the relations expressed by in general, $\Phi=f(\mu_a, \mu_s',\omega)$ are utilized. At this time, since $\omega$ is a controllable parameter, $\Phi$ is detected with respect to the two or more different angular frequencies $\omega$. Then, the absorption coefficient $\mu_a$, the scattering coefficient $\mu_s'$, and the effective attenuation factor $\eta$ can be obtained from the two simultaneous equations as a function of $\omega_1$ and $\omega_2$. Note that here, the fact that the absorption coefficient or the transport scattering coefficient does not depend on the modulated angular frequency $\omega$ of modulated light is utilized.

Sinusoidal modulated light having two or more different angular frequencies or, modulated light including two or more angular frequency components may be used in the above measurement. Further, repeating pulsed light and repeating square wave light can be utilized since they have a fundamental frequency component and higher-order frequency components which are integer times higher than the fundamental one.

Further, in the above measurement, a specific absorptive constituent or a specific scattering constituent in the scattering medium can be measured and determined, using light having two or more different wavelengths. The measurement is substantially the same as the measurement in section (t) except that the modulated light having two or more different angular frequencies is used. Note that the light attenuation factor $\eta$ described in section (2) is not needed to be considered since it has no relation with the phase delay $\Phi$.

As is apparent from the above explanation, the modulated light method described here uses one photodetection distance, so that there is an advantage that the configuration of the measurement apparatus and arithmetic process are simplified. In particular, the method and apparatus which are effective in imaging or measurement of a cross sectional image described in section (1) can be provided using this modulated light method. Note that the principle of the imaging and measurement of a cross sectional image is substantially the same as that in section (1), so that the detailed description for this is omitted. Further, it is apparent that if three or more modulated angular frequencies are utilized, the measurement accuracy is improved. Furthermore, the modulated light method and the method for measuring at different photodetection distances, which is described before, can be used together.

(4) Measurement of Relative Value of Internal Information.

The absolute value measurement has been explained in sections (1) to (3). However, time-change in absorption coefficient measured as a relative value, and a spacial distribution of absorption coefficient are effective information. In the relative value measurement, if the predetermined parameters are properly selected, the number of simultaneous equations which are required for obtaining unknown values may be reduced.

For example, when dual-wavelength spectroscopy is utilized, if the transport scattering coefficients $\mu_s'$ with respect to two different wavelengths are considered to be constant, the transport scattering coefficient $\mu_s'$ can be treated as a constant value and the number of the simultaneous equations may be reduced. If $\mu_a \ll \mu_s'$, using the approximation, the equations may be simplified. Further, the relative values of the internal information can be measured with one photodetection distance, at different times, at different points, or using light having different wavelengths. The light attenuation factor $\eta$ described in section (2) can be eliminated by taking a ratio of two optically detected signals. Consequently, the relative measurement utilizing time differential waveform of the photon current J or the approximate absolute measurement can be made possible.

The above can be understood easily by modifying the relations expressed by the equations (3.2) to (3.8) and the equations (3.13) to (3.19) into simplified forms. A method and means using such approximation have a weakness in that the measurement error is somewhat increased due to approximations, but it has the big advantage that imaging in two dimensional measurement or measurement of cross sectional image can be simply performed.

The embodiments of the present invention will now be described with reference to the accompanying drawings below. In the description of drawings, the same elements are represented by the same reference numerals and the repetitive description on the same elements is omitted.

First Embodiment

Figure 13:
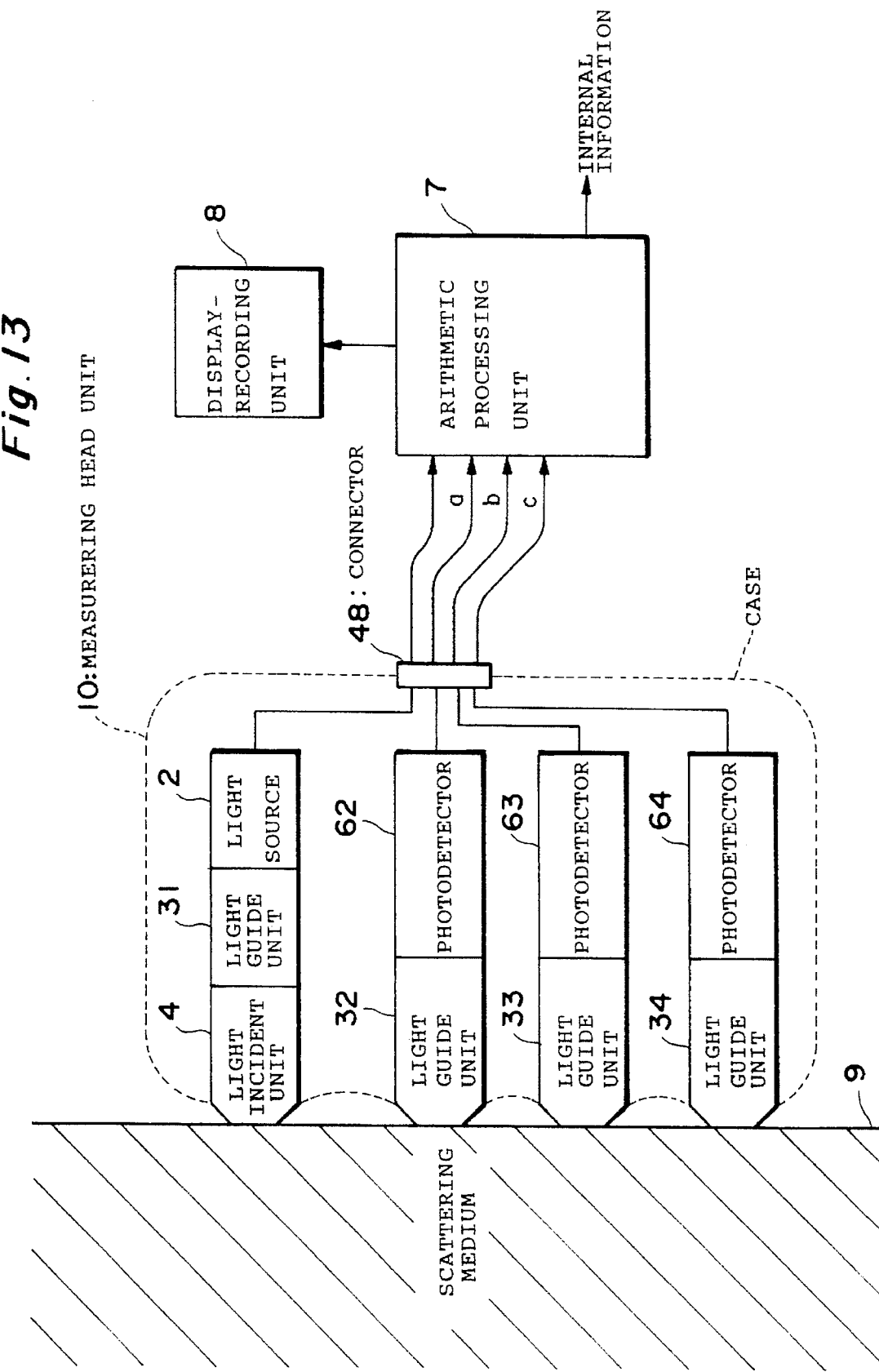
FIG. 13 is a view showing a configuration of an apparatus of the first embodiment.

FIG. 13 shows the first embodiment of the present invention and shows a configuration of a method and apparatus for measuring internal information in a scattering medium 9, for example, an absolute value of an absorption coefficient or a transport scattering coefficient. In this configuration, three detected signals corresponding to the three kinds of photodetection distances are obtained, so that the three relations as described above, e.g., the three simultaneous equations are obtained. Accordingly, this embodiment can be applied to measurements where the number of the unknown values is three or less, and the typical application of this embodiment is "absolute value measurement taking light attenuation on the surface into consideration", the operation principle of which already explained.

A measuring head unit 10 is used closer to or in contact with the surface of the scattering medium 9 which is an object to be measured, and a light incident unit and photodetectors are contained in a box or a case. Light having a predetermined wavelength from a light source 2 is guided to a light incident unit 4 through a light guide unit 31 such as an optical fiber. The light incident unit 4 makes light having various incident angle components to be incident on a predetermined portion of the surface of the scattering medium, which will be described later. In this case, light radiated from the light source 2 may have any type of waveform, such as continuous light, pulsed light, square wave light, modulated light etc. For the light source, a laser diode, a light emitting diode, a HeNe laser etc. can be used.

The light incident on the scattering medium 9 through the light incident unit 4 is diffused during propagation in the scattering medium 9, and some light components pass through light guide units 32, 33 and 34 such as optical fibers and are detected by photodetectors 62, 63 and 64 and converted into electrical signals. For the photodetector, various kinds of photodetectors having a sensitivity to light having a predetermined wavelength, such as a phototube, a photomultiplier, a photodiode, a pin photodiode, an avalanche photodiode etc. can be used. An arithmetic processing unit 7 uses the detected signals obtained by the photodetectors 62, 63 and 64 to extract the predetermined parameters, which are the primary information and processes the primary information to calculate internal information of the scattering medium, which is secondary information and outputs this internal information. For this arithmetic processing, in general, three kinds of photodetection distances set beforehand, or three kinds of photodetection distances obtained by another method beforehand are used as known values. Further, for these arithmetic processing, a synchronizing signal synchronized with the light source is utilized if necessary. Further, the result of arithmetic is displayed or recorded by a display-record unit 8 if necessary.

Here, the arithmetic process to obtain the primary information and the secondary information will be explained in detail. When light having various kinds of incident angle components is incident on the scattering medium from the light incident unit 4, as already described above, it can be considered that an equivalent point light source or a group of equivalent point light sources is generated near or on the surface of the scattering medium and light from this point light source is diffused during propagation in the scattering medium. Accordingly, the above-described relations, e.g., the relations expressed by the equations (3.2) to (3.8), hold for the primary information obtained by processing the signals detected by the photodetectors 62, 63 and 64, that is, relations between the predetermined parameters and the absorption characteristic and the scattering characteristic on the diffusion-propagation path of the light diffused during propagation. Therefore, the predetermined parameters which are the primary information are processed based on such relations to calculate the internal information in the scattering medium, which is the secondary information, for example, the absorption coefficient $\mu_a$ or the transport scattering coefficient $\mu_s'$.

The parameters used in the above measurement are various kinds of predetermined parameters expressed in two ways, which are derived from the photon currents $J_g$ and $J_\phi$, that is, the average optical pathlength $<L>$, the time differential value of the photon current J, the time integral value of the photon current J etc. Note that here a measured first signal taking the light attenuation factor η into consideration is considered here. For example, the photon current J is given by the equations (3.2) and (3.3) and the optically detected signal taking the light attenuation factor η into consideration can be expressed, e.g., as equation (4.2). Similarly, equations which are functions of other predetermined parameters can be obtained. As described above, the predetermined parameters which are the primary information can be obtained from the optically detected signals by arithmetic processing based on the equations (3.2) to (3.8).

The light incident unit 4 causes light having various kinds of incident angle components to be incident on the predetermined area of the surface of the scattering medium to generate an equivalent point light source or a group of equivalent point light sources near or on the surface of the scattering medium, and as described above, it is desired that the angle distribution of incident light is uniformly distributed within a range 0° to 30°. Further, if it is uniformly distributed within a range 0° to 45°, the accuracy is further improved. Examples of configurations of the light incident unit are shown in FIGS. 14–18, which will now be explained in detail.

Figure 14:
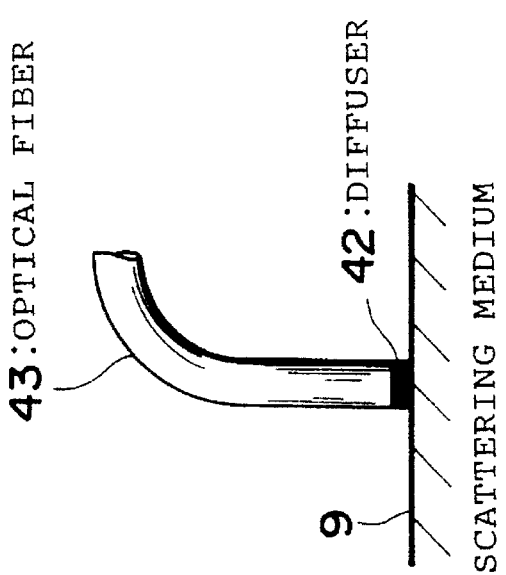
FIGS. 14–16 are views showing a detailed configuration of a light incident portion.

FIG. 14 shows a light incident unit using a lens. A lens 41 is placed at the edge of a tube-like box or a tube-like case 49. Collimated light or a substantially collimated light beam is incident on the lens. Then, the beams are gathered by the lens 41 and incident on the scattering medium 9. The lens 41 is installed within an end of the tube-like case 49 and arranged so that the surface of the scattering medium 9 is located at a focal point of the light incident unit or near the focal point when an end of the tube-like case 49 contacts the scattering medium. In this case, the angle distribution of light incident on the scattering medium is determined by a diameter of the lens, the focal length of the lens, a diameter of beam, and divergent angle of beam, so that as they are suitably selected, light is able to have various angle constituents, for example, within a range 0° (normal incidence) to 30°. In this configuration, various kinds of lenses such as a rod lens, Fresnel lens can be used other than the ordinary lens. Further, the light incident on the lens 41 may be light guided with an optical fiber.

Figure 15:
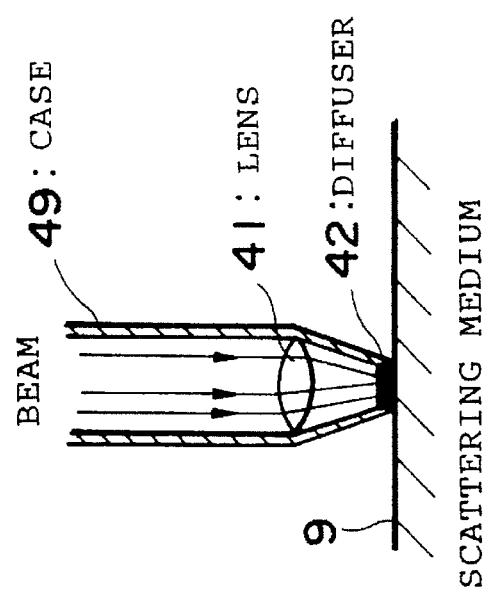

FIG. 15 shows a light incident unit in which a diffuser 42 is placed at an end of the tube-like case 49. Light is caused to be incident on the scattering medium 9 through the diffuser 42 placed at the end of the tube-like case 49, and the other portions are the same as those of the configuration of FIG. 14. In this configuration, light having various incident angle components obtained by the lens 41 is further diffused by the diffuser 42, so that light having many kinds of incident angle components is made to be incident on the scattering medium. For example, in the case of a diffuser for complete diffusion, light having incident angle components in a range of 0° to 90° (to be semi-spherical) is incident on the scattering medium 9. Note that in this configuration, the lens 41 may be omitted. Further, in this configuration, a group of equivalent point light sources can be generated at a predetermined portion of substantially the same area as the diffuser on the surface of the scattering medium.

Figure 16:
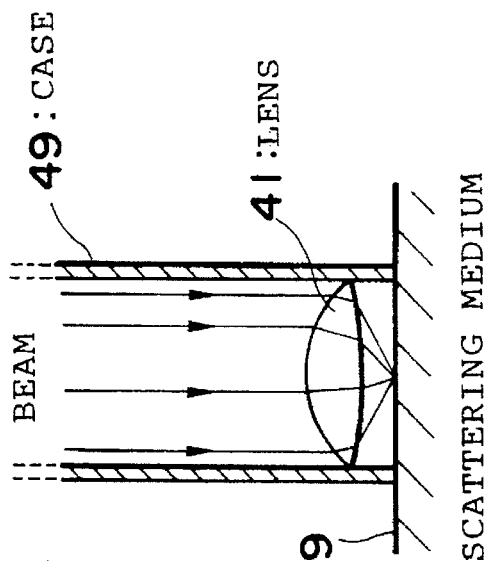

FIG. 16 shows a light incident unit in which a diffuser 42 is placed at an end of an optical fiber 43. Light propagating in the optical fiber 43 is diffused at the diffuser 42 and light having various incident angle components, which is diffused at the diffuser 42 is incident on a scattering medium 9. Angle distribution of light which is able to be incident on the optical fiber or angle distribution of light which is able to emerge from the optical fiber can be estimated from the numerical aperture of the optical fiber. For optical fibers on the market, only light having angle components of 30° or below emerges from the optical fiber. However, with the configuration in which the diffuser is placed as shown in FIG. 16, light having large number of angle components can be made to be incident on the scattering medium. Further, with this configuration, the diffuser 42 can be placed on the surface of the scattering medium 9 and light from the optical fiber 43 is caused to be incident on the diffuser 42.

Figure 17:
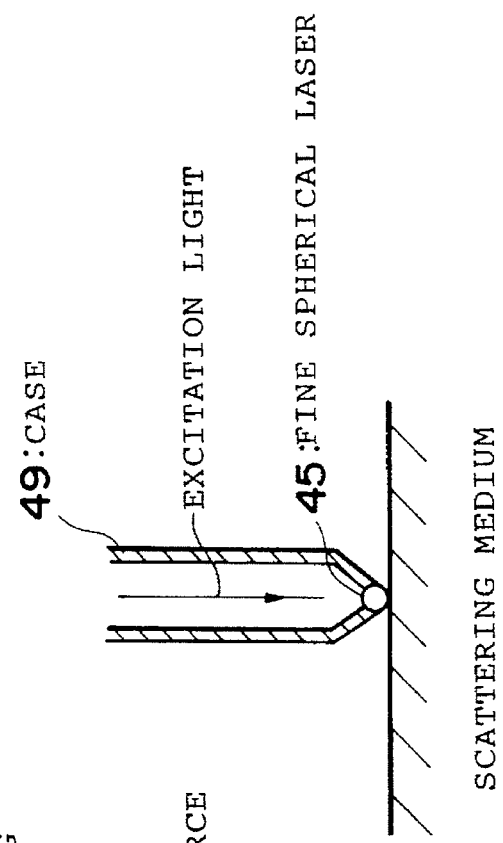
FIGS. 17 and 18 are views showing a detailed configuration of a light incident portion.

FIG. 17 shows a device for causing light from a light source 2 provided inside an integrating sphere 44 which is placed on the surface of a scattering medium 9 to be incident on the scattering medium 9 using an opening of the integrating sphere 44. Light from the light source 2 is reflected multiple times in the integrating sphere 44, and light having various angular components emerges from the opening, to be incident on the scattering medium. Note that the light source is electrically controlled through a connector on the integrating sphere.

Figure 18:
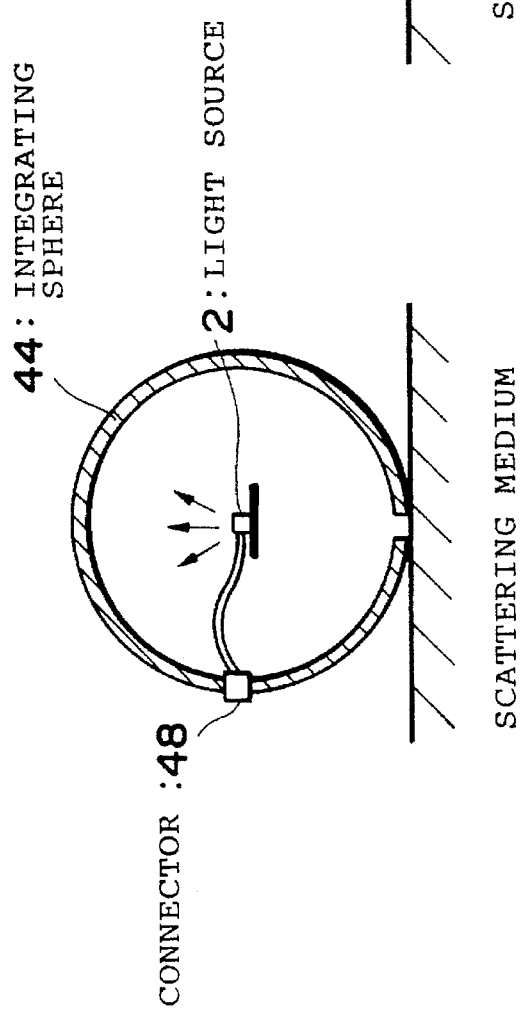

FIG. 18 shows a light incident unit in which a fine spherical laser 45 is put on an end of a tube-like case 49. Recently, laser oscillation from a solid polyethylene sphere in which laser dye is doped having a diameter of 20 μm was observed. Light from the fine spherical laser has various angle components, so that this light is directly caused to be incident on the scattering medium.

As described in detail, the light incident unit may have any configuration as long as it can make light having various light angle components to be incident on the scattering medium. Further, the diffuser 4 may have any configuration, e.g., opal glass, as long as it diffuses light having a predetermined wavelength.

Further, in the above embodiment, a 3-channel photodetecting system is used but as a modified example, a method using a light source of 2 channels or more, a method for measuring with a photodetecting system of 4 channels or more which is placed on plural locations etc. can be used. In these cases, there are a method for lightening a light source in time series and a method using light sources having different wavelengths etc. In the measurement utilizing a principle of dual-wavelength spectroscopy, two or more light components having different wavelengths are incident and the predetermined parameters, which are the primary information, are obtained with respect to each wavelength. Then, the internal information in the scattering medium, which is the secondary information, is obtained by processing the parameters. Examples of such methods include a method of using two or more light components having different wavelengths and synchronizing with this, obtaining an optically detected signal with respect to each wavelength, a method for causing two or more light component having different wavelengths to be incident at the same time and selecting a wavelength by a photodetector to obtain an optically detected signal, a method using a plurality of apparatus shown in FIG. 13 with respect to each wavelength etc.

Further, the above methods can be applied to the relative value measurement. In this case, as described above, the number of relations may be reduced. For example, there is a method utilizing two photodetection distances. Furthermore, with the configuration of FIG. 13, if the measurement head unit 10 is made to be scanned (not shown) over the scattering medium 9, a spatial distribution of internal information in the scattering medium can be measured. In this case, there is a simple method for scanning the measuring head unit 10 by hand.

Second Embodiment

An apparatus of the second embodiment is a modification of the measuring head unit 10 of the first embodiment which was explained with FIG. 13, and is used for the measurement of internal information in a human head. In particular, this apparatus is for the measurement and/or the monitoring of the concentration of oxyhemoglobin or the degree of oxygen saturation of hemoglobin in a human brain. If the structure of the apparatus is changed slightly, the apparatus can be used, for example, to measure or monitor the concentration of oxyhemoglobin in a muscle of a human who runs a marathon.

Figure 19:
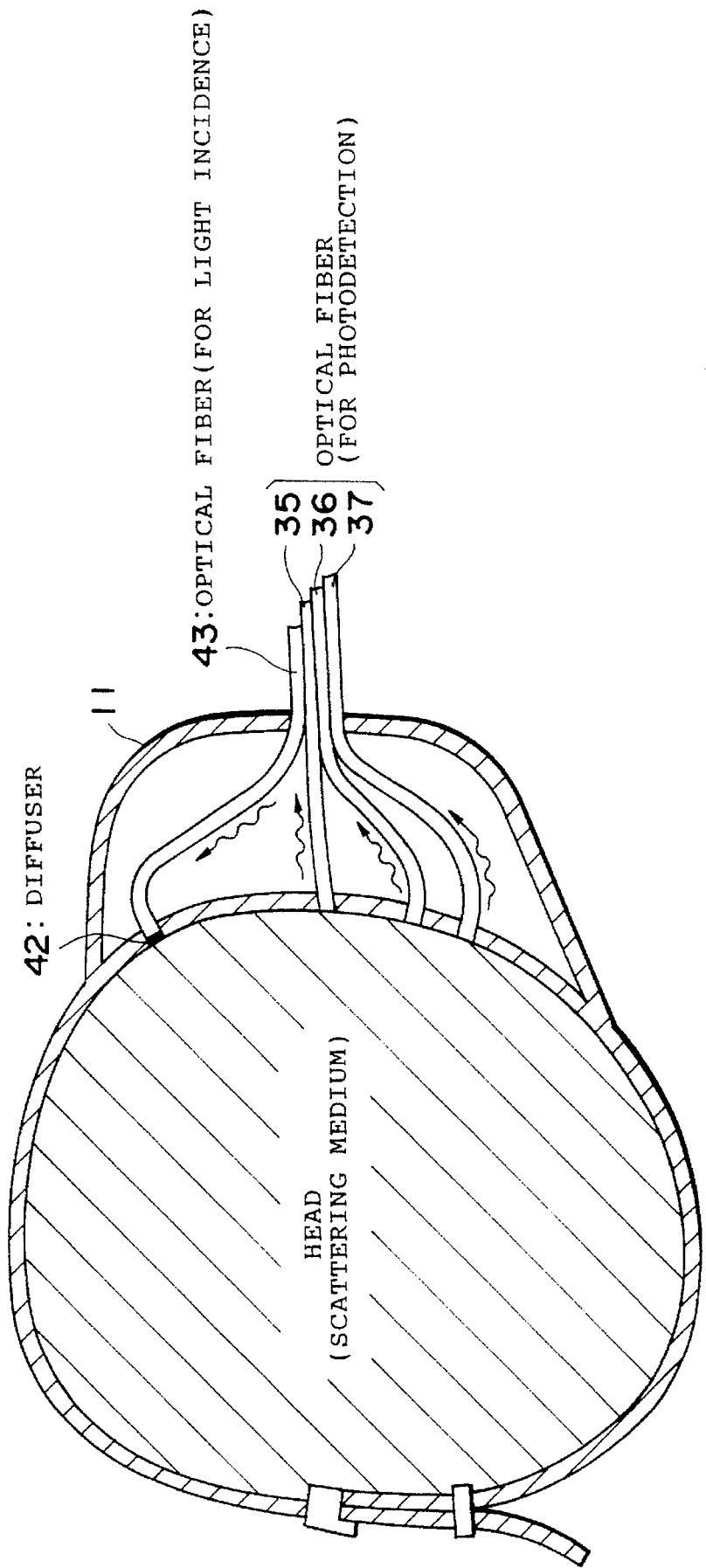
FIG. 19 is a view showing a configuration of an apparatus of the second embodiment.

FIG. 19 shows a detailed configuration of a measuring head unit of the second embodiment. A container 11 with an adapting band is put on a head like a headband, and the degree of oxygen saturation of hemoglobin in a brain is measured. The apparatus of this embodiment uses light having two predetermined wavelengths $\lambda_1$ and $\lambda_2$, and the operation is substantially the same as the first embodiment. Note that in FIG. 19, only the measuring head unit is shown and a light source unit, a photodetecting unit, an arithmetic processing unit, a record-display unit etc. are omitted. Further, in FIG. 19, the components which have the same function as described in FIG. 13 are represented by the same reference numerals.

Light having a predetermined wavelength $\lambda_1$ or $\lambda_2$ from a light source unit (not shown) is guided to a measuring unit passing through an optical fiber 43. Then light is incident on a head which is a scattering medium through a diffuser 42 put on an end of the optical fiber. Accordingly, light having various incident angle components is incident on a predetermined portion on a surface of the scattering medium. At this time, the two wavelengths should properly be selected so that the absorption coefficients of the two wavelengths are different for a specific absorptive constituent which is an object to be measured. Light diffused during propagation in the head which is a scattering medium is received by optical fibers 35, 36 and 37 and guided to three photodetectors (not shown) and converted into electric signals.

Figure 20:
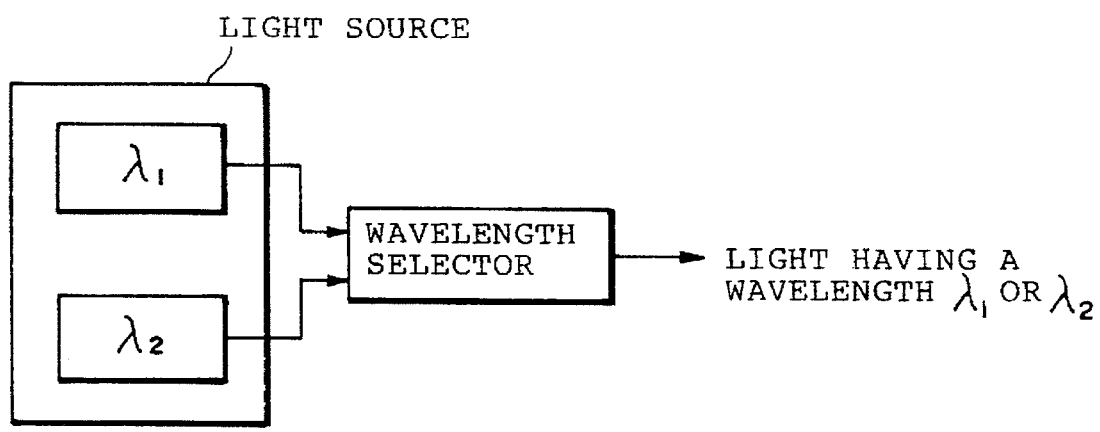
FIGS. 20 and 21 are views illustrating a method for switching light having a different wavelength and a method for mixing lights having a different wavelength.
Figure 21:
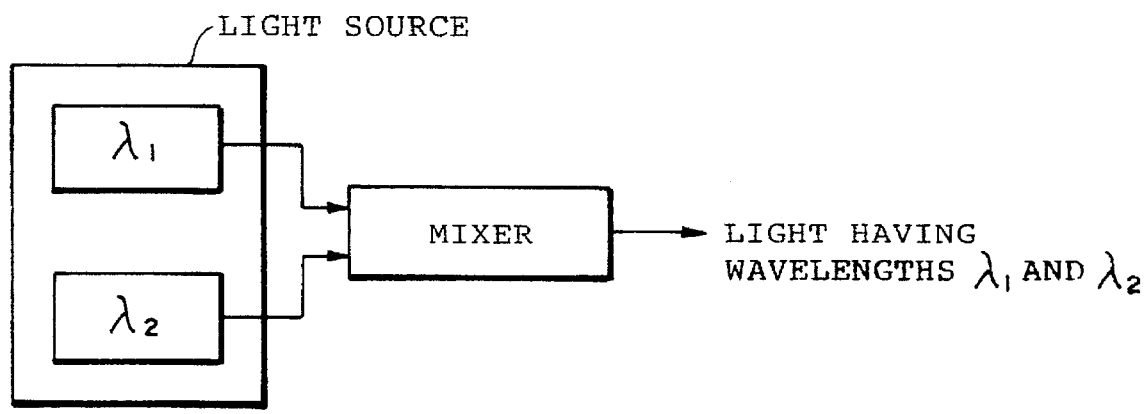

Light from the light source is guided to the optical fiber 43 utilizing a method for switching two light components having different wavelengths by a wavelength selector as shown in FIG. 20, or a method for mixing two light components having different wavelengths as shown in FIG. 21. The band pass filter in front of the photodetector (not shown) is switched in accordance with the wavelength to detect light having a predetermined wavelength. In this case, a method for lightening with two light components having different wavelengths in time series and synchronizing with this, detecting light having a respect wavelength can be possible. Further, during relative value measurement, light having two components each having different wavelength are mixed and incident on the scattering medium, and two photodetectors of the three photodetectors shown in FIG. 19 detect light having a wavelength $\lambda_1$ and the other photodetector detects light having a wavelength $\lambda_2$.

Furthermore, in the above configuration, the light source and the photodetector can be put in the container 11. In this case, a power supply and a signal processor are electrically connected through a connector and cables.

In the above-described configuration of the second embodiment, the unknown values are the absorption coefficients $\mu_{a1}$ and $\mu_{a2}$ with respect to the wavelengths $\lambda_1$ and $\lambda_2$, the transport scattering coefficients $\mu_{s1}'$ and $\mu_{s2}'$ with respect to the wavelengths $\lambda_1$ and $\lambda_2$, and the light attenuation factor $\eta$, and then the number of unknown values are five. Therefore, in order to carry out the absolute value measurement, five or above optically detected signals are needed and based on the five relations with respect to the predetermined parameters, the internal information, which is the secondary information, e.g., the degree of oxygen saturation of hemoglobin is calculated.

Further, if the transport scattering coefficients with respect to the wavelengths $\lambda_1$ and $\lambda_2$ are considered to be equal, that is, the number of unknown values is four for $\mu_{s1}'=\mu_{s2}'$, the internal information can be calculated from the four or more optically detected signals. Furthermore, if the light attenuation factor $\eta$ can be neglected, the number of unknown values is three, and the internal information can be calculated from the three or more optically detected signals. In the case of relative measurement such as time-change in internal information, the number of required optically detected signals may be reduced.

The various arithmetic processes for the optically detected signals are carried out with an arithmetic processing unit (not shown). The arithmetic processes are substantially the same as the first embodiment, and can be performed at high speed using a computer.

Third Embodiment

Figure 22:
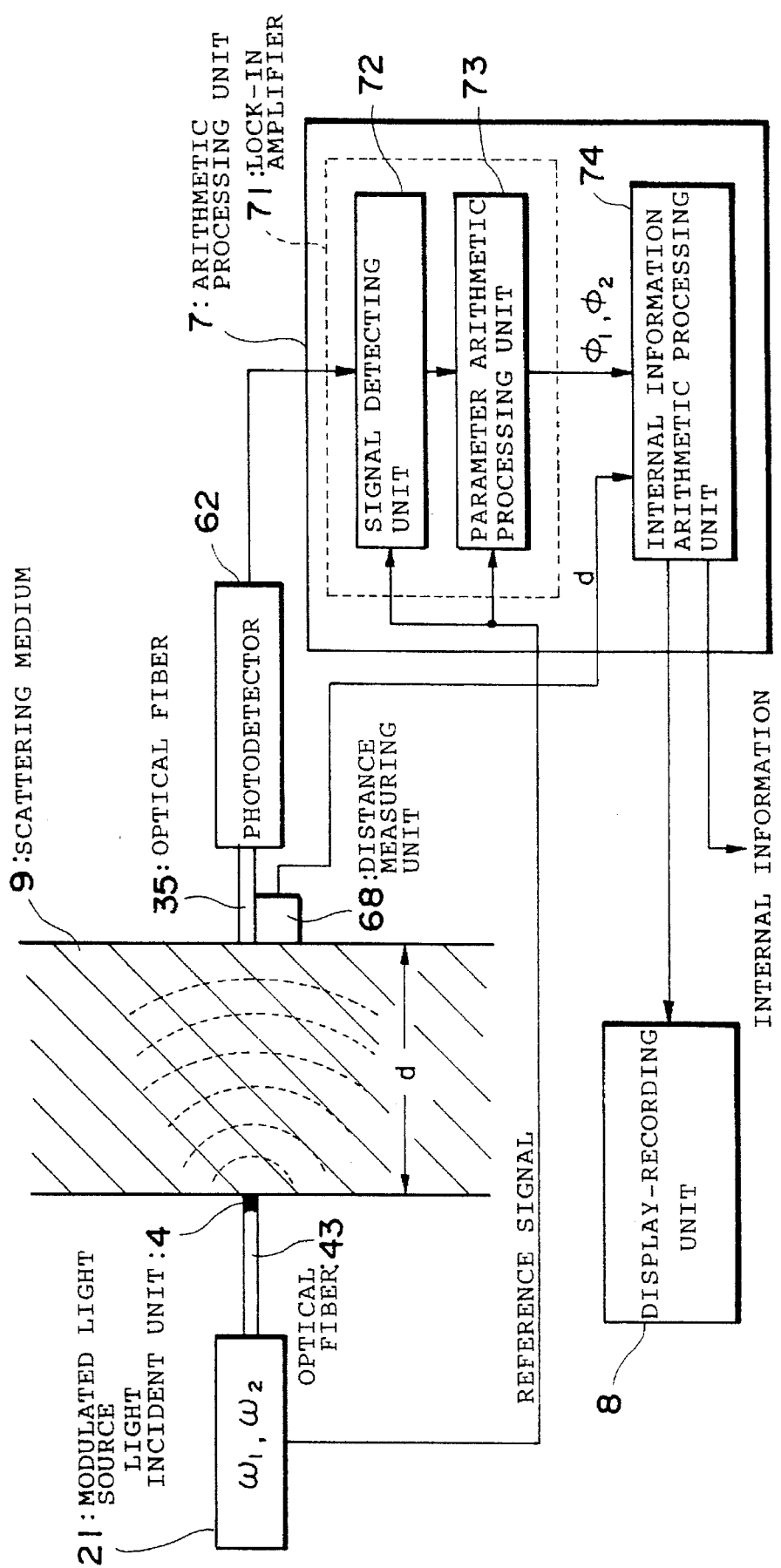
FIG. 22 is a view showing a configuration of an apparatus of the third embodiment.

FIG. 22 shows the third embodiment of the present invention, and shows a method for measuring internal information in a scattering medium 9, e.g., a concentration of an absorption coefficient or a specific absorptive constituent by causing modulated light to be incident on the scattering medium. In FIG. 22, the components which function or operate the same as components shown in FIG. 13 and FIG. 19 are represented by the same reference numerals used in FIG. 13 and FIG. 19. Modulated light having a predetermined wavelength generated from a modulated light source 21 has two predetermined angular frequencies $\omega_1$ and $\omega_2$, and is guided to a light incident unit 4 through an optical fiber 43. Here, the diffuser is utilized as a light incident unit.

Figure 23:
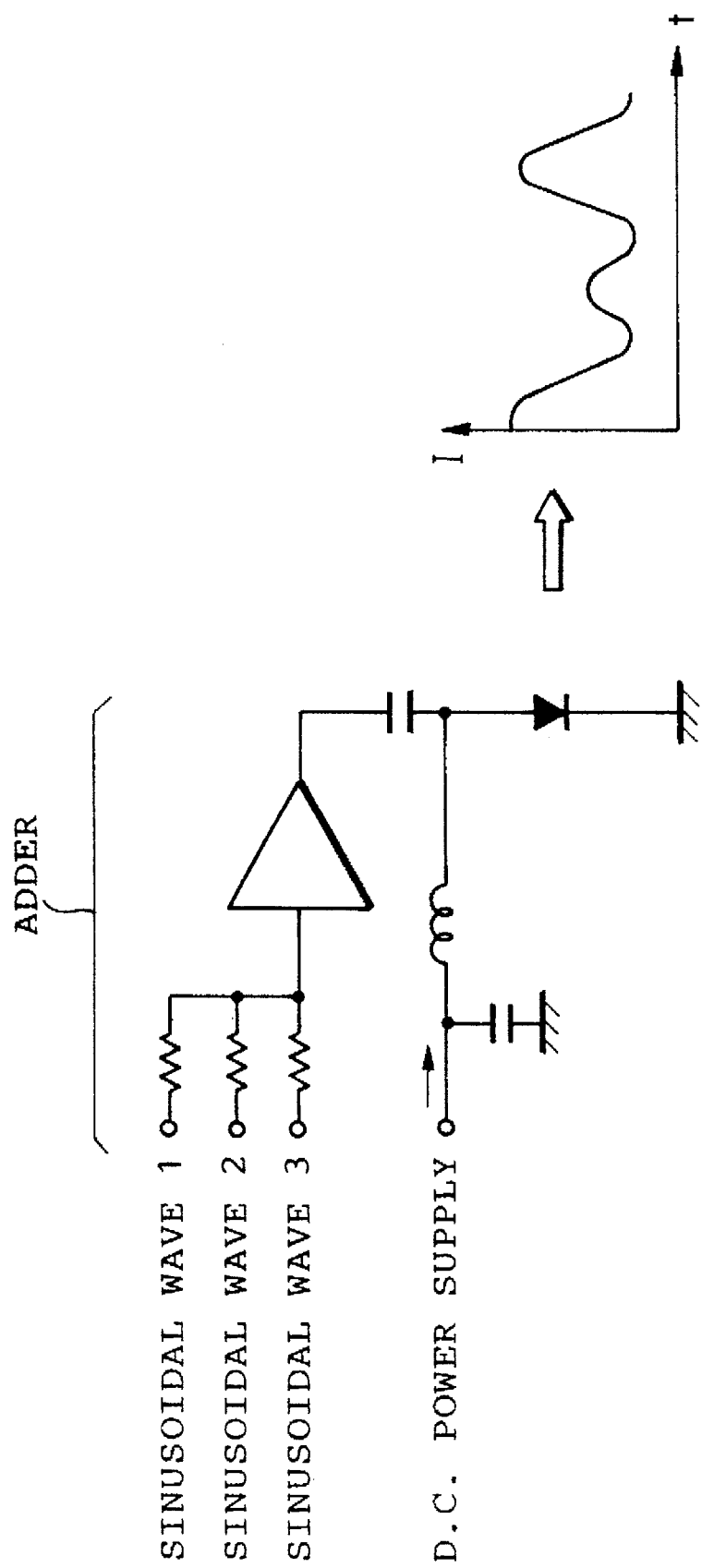
FIG. 23 is a view illustrating a method for generating modulated light with a laser diode.

Modulated light having two or more predetermined frequency components can be generated utilizing the current modulation of a laser diode as shown in FIG. 23. In this case, current driving the laser diode is generated by adding two or more sinusoidal waves having a predetermined frequency component with an adder. Modulated light having two or more predetermined frequency components can be generated by mixing two or more modulated lights having different modulated frequencies. As already explained above, in the measurement, repeating pulsed light or repeating square wave light can be used.

The light incident unit 4 is for making light having various angle components to be incident on the surface of the scattering medium, and there are many structures for the light incident unit 4 as explained in the first embodiment. Light incident on the scattering medium 9 through the light incident unit 4 is diffused during propagation in the scattering medium 9. Some of the light components pass through an optical fiber 35 and are converted into the electric signal by a photodetector 62. A lock-in amplifier 71 constituting an arithmetic processing unit 7 processes the optically detected signal to detect a phase delay $\Phi$ of the signal having a predetermined frequency component, which is the primary information. At this time, a signal having an angular frequency $\omega$ in synchronization with the modulated light is utilized as a reference signal of the lock-in amplifier 71. In particular, a signal detecting unit 72 constituting the lock-in amplifier 71 first detects a signal having a predetermined angular frequency component $\omega_1$ from the optically detected signal, and a parameter detecting unit in the next state detects a predetermined parameter, such as the phase delay $\Phi_1$. Next, the reference signal of the lock-in amplifier 71 is switched and the phase delay $\Phi_2$ with respect to the predetermined angular frequency $\omega_2$ is detected. Note that the lock-in amplifier 71 can be replaced with an apparatus comprising various circuits having equivalent functions to the lock-in amplifier 71.

An internal information arithmetic processing unit 74 calculates internal information in the scattering medium, which is the secondary information, e.g., an absorption coefficient $\mu_a$ or a transport scattering coefficient $\mu_S'$ based on the simultaneous relations which are relations between the phase delay $\Phi$ which is the primary information and the absorptive characteristic and the scattering characteristic on the diffusion-propagation path of the diffused and propagating light, e. g., the relations shown in the equations (3.18) and (3.19). A distance d measured by a distance measuring unit 68 is used for the arithmetic process if necessary. The results are displayed and recorded or outputted if necessary.

With the above configuration, if the measurement is carried out with respect to light having a wavelength $\lambda_1$ and light having a wavelength $\lambda_2$, the absorption coefficients $\mu_{a1}$ and $\mu_{a2}$ with respect to each wavelength and the transport scattering coefficients $\mu_{S1}'$ and $\mu_{S2}'$ with respect to each wavelength can be obtained. Accordingly, for example, determination of a specific absorptive constituent and a specific scattering constituent or a degree of oxygen saturation of hemoglobin can be calculated. Further, if light having three or more wavelengths is utilized, improvement in the measurement accuracy or measurement of specimens which have background absorption is made possible. Furthermore, a photodetecting system of a plurality of channels can be utilized.

In such dual-wavelength spectroscopy, the absolute values of transport scattering coefficients $\mu_{S1}'$ and $\mu_{S2}'$ with respect to the two wavelengths can be obtained, which is a big advantage and which is not achieved in the prior art. Therefore, even though the assumption in the conventional dual-wavelength spectroscopy that the difference of the scattering coefficients of the scattering constituents with respect to light having two different wavelengths is extremely small, does not hold, the measurement method and apparatus of the present invention can perform the measurement with high accuracy. As described above, the measurement method and apparatus according $\mu_S'$ the present invention can largely improve the measurement accuracy and expand the application fields against the conventional dual-wavelength spectroscopy. Note that when the transport scattering coefficients $\mu_S'$ with respect to the two different wavelengths can be considered to be equal, the simpler equations or relations can be utilized.

With the above-described configuration, if the light incident position and the photodetection are relatively scanned (not shown) over the scattering medium 9, the spatial distribution of the internal information can be measured. Further, it is apparent that if the measurement is carried out at a different time, time-wise variation in the internal information can be measured. This sort of measurement can be utilized to monitor the amount of oxygen in the brain or in other applications. If the absorption coefficient $\mu_a$ or the transport scattering coefficient $\mu_S'$ obtained above is a line integral value along the diffusion-propagation path corresponding to the light incident position and the photodetection point, cross sectional images as often seen in x-ray CT can be reconstructed, utilizing data.

In general, such arithmetic process can be performed at high speed with a computer unit which comprises a memory, a display and other components.

Fourth Embodiment

Figure 24:
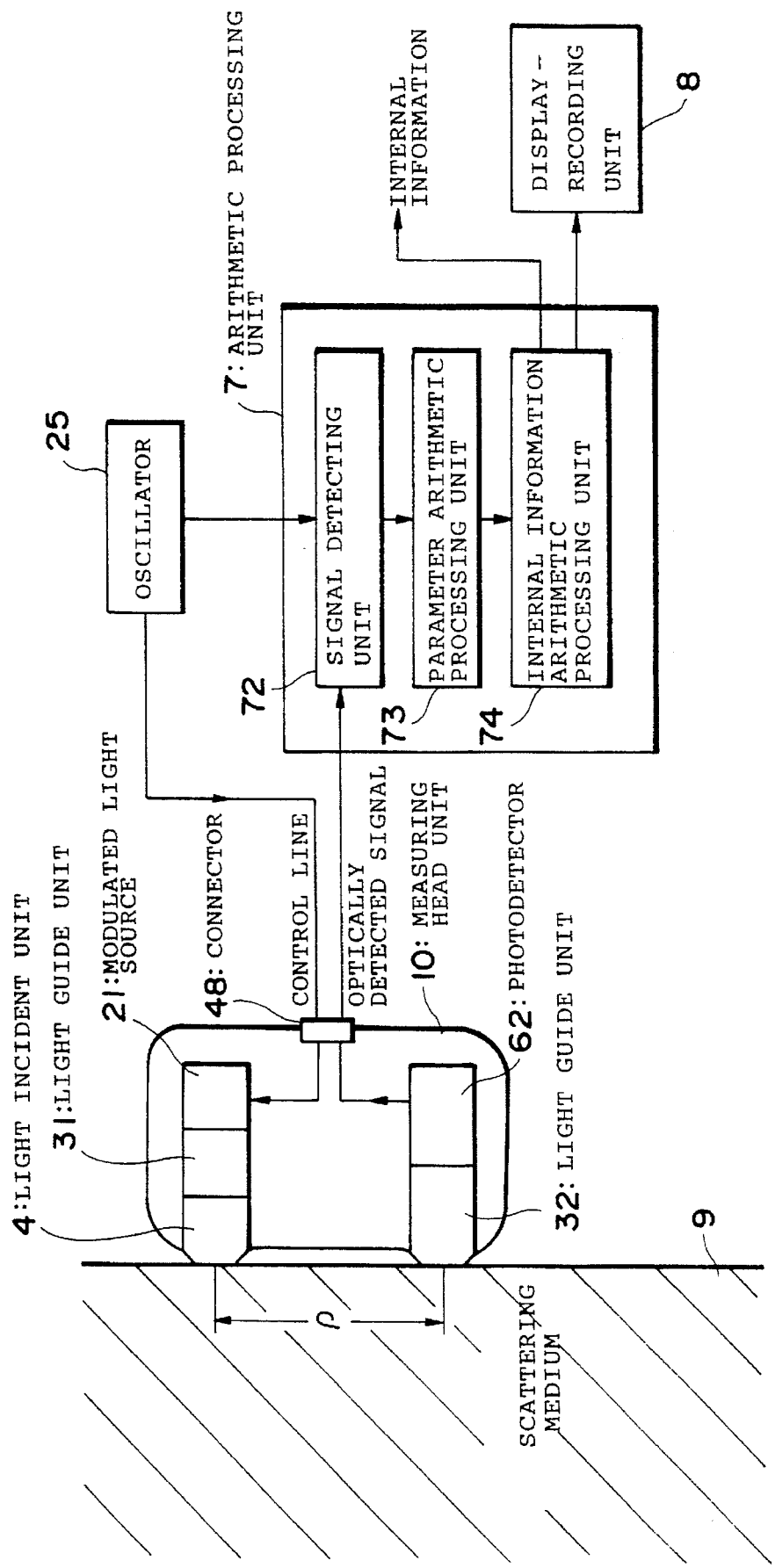
FIG. 24 is a view showing a configuration of an apparatus of the fourth embodiment.

FIG. 24 shows a configuration of the fourth embodiment of the present invention and which used for the measurement of internal information in a living body or a human head. In particular, the concentration of oxyhemoglobin or degree of oxygen saturation of hemoglobin in a brain or a muscle can be measured or monitored. In this embodiment, a modulated light method is applied to the reflection measurement. Note that in FIG. 24, the components which perform the same functions and operations as the ones shown in FIG. 13, FIG. 19 and FIG. 22 are represented by the same reference numerals.

Modulated light has two predetermined angular frequencies $\omega_1$ and $\omega_2$ generated from a modulated light source 21 and is guided to a light incident unit 4 through a light guide unit 31 such as an optical fiber. The light incident unit 4 causes light having various angle components to be incident on the surface of the scattering medium, and there are many structures for the light incident unit 4 as explained in the first embodiment. Light incident on the scattering medium 9 through the light incident unit 4 is diffused during propagation in the scattering medium 9. Some light components pass through a light guide unit 32 and are converted into an electric signal by a photodetector 62. As in the third embodiment, an arithmetic processing unit 7 processes the optically detected signal to detect a phase delay $\Phi$ of the signal having a predetermined frequency component, which is the primary information, and calculates internal information in the scattering medium, which is the secondary information, e.g., an absorption coefficient $\mu_a$ or a transport scattering coefficient $\mu_S'$. At this time, a signal having an angular frequency $\omega$ in synchronization with the modulated light is utilized as a reference signal. Further, the results are displayed and recorded or outputted if necessary.

To generate modulated light having two or more predetermined frequency components, a method for generating modulated light using current modulation of a laser diode, and a method for generating modulated light by mixing two modulated light component having different modulated frequencies may be used. As already explained above, repeating pulsed light or repeating square wave light can be used.

In this embodiment, like in the third embodiment, by using light having a wavelength $\lambda_1$ and light having a wavelength $\lambda_2$, the absorption coefficients $\mu_{a1}$ and $\mu_{a2}$ with respect to each wavelength and the transport scattering coefficients $\mu_{s1}'$ and $\mu_{s2}'$ with respect to each wavelength can be obtained. Accordingly, for example, determination of a specific absorptive constituent and a specific scattering constituent or a degree of oxygen saturation of hemoglobin can be calculated. Further, if light having three or more wavelengths is utilized, improvement in the measurement accuracy or measurement of specimens which have background absorption are made possible. Furthermore, a photodetecting system of a plurality of channels can be utilized. If the transport scattering coefficients $\mu_s'$ corresponding to the two different wavelengths are considered to be equal, the simple equations or relations can be utilized. The above methods can be applied to the relative value measurement. In this case, as described above, the number of relations may be reduced. Furthermore, with the configuration of FIG. 24, if the measurement head unit 10 is scanned (not shown) over the scattering medium 9, a spatial distribution of internal information in the scattering medium can be measured. In this case, there is a simple method for scanning the head measuring unit 10 by hand.

In general, such arithmetic processing can be performed at high speed with a computer unit which comprises a memory, a display and other components. The head measuring unit 10 may be placed on a band as shown in the second embodiment.

Fifth Embodiment

FIG. 25 shows a configuration of a cross sectional image measuring apparatus for a scattering medium of the fifth embodiment. In the fifth embodiment, the scattering medium which is an object to be measured is rotated and alternatively, a modulated light incident unit and a photodetector may be rotated and scanned so that a measuring line connecting a modulated light incident position and a photodetection point cross in all directions in a predetermined cross section of the scattering medium. Then, the secondary information obtained is further processed to reconstruct the cross sectional image with respect to various internal information.

The fundamental portions of the structure shown in FIG. 25 are the same as the ones shown in FIG. 22 but a portion for holding an object 92 to be measured, a wavelength selector 22, a light guide 38, a signal processing unit 75 for reconstructing a cross sectional image etc. are different. A light source 2 generates two modulated light components each having a predetermined wavelength in synchronization with a signal from an oscillator. The modulated light has two predetermined angular frequencies $\omega_1$ and $\omega_2$, and its light intensity I(t) is given by, e.g., $I=I_0(2+M_1\cos\omega_1 t+M\omega\cos\omega_2 t)$.

Such modulated light is selected by the wavelength selector 22 and modulated light having a wavelength $\lambda_1$ or $\lambda_2$ passes through an optical fiber 43 and is incident on an object 92 to be measured which is surrounded by an interface material 91. The interface material 91 is a liquid medium or a jelly-like medium having substantially the same refractive index and scattering coefficient as the object 92 to be measured. The interface material 91 is surrounded by a thin film container 93 in which light reflection is small. Accordingly, light incident on the container 93 containing the interface material 91 is hardly reflected at a boundary. Further, if the inner and outer surfaces of the thin film container 93 are rough surface, incident light has components traveling in all directions. Diffused light is diffused during propagation inside the interface material 91 and the object 92 to be measured and reaches the photodetecting unit. A light guide 38 is in the photodetecting unit, and the detected light is incident on a photodetector 62 through the light guide 38. Here, it is desirable for the inside of the container 93 containing the interface material 91 around the opening of the light guide 38 to be a light absorptive medium, so that light reflections from the inside of the container will not affect measurement and precise measurement can be performed.

Note that the object 92 to be measured is relatively rotated against the optical fiber 43, the light guide 38, the interface material 91 and the container 93. Accordingly, the container 93 is needed to have such structure that the exterior of the cross section of the container 93 is circular but the interior changes its shape in accordance with the object 92 to be measured so that no gap is formed when the object 92 to be measured is rotated. As such structure, for example, as shown in FIG. 25, a container may be formed to surround the periphery of the object 92 to be measured, separate containers may be formed for each of the light incident side and the light emerging side may be formed, as shown in FIG. 26. In either case, for the interface material 91 should be closely spaced to the openings for light incidence and photodetection and that the interior is closely attached to the object 92 to be measured.

With the above-described structure, first the optically detected signal with respect to a predetermined wavelength $\lambda_1$ is processed by the arithmetic processing unit in the same way as the fourth embodiment to calculate the secondary information, e.g., the absorption coefficient $\mu_{a1}$ at a wavelength $\lambda_1$. Such secondary information is data obtained by measuring a predetermined cross section of the object to be measured in various directions, for example 360° data measured in all directions every 1° of rotation angle. Since such secondary information can be considered as a line integral value of the absorption coefficient along the line connecting between the light incident position and the photodetection point, that is, along the diffusion-propagation path, the signal processing unit 75 reconstructs the image as often seen in x-ray CT, for example, to calculate the cross sectional image of the absorption coefficient at a wavelength $\lambda_1$. This is stored in a first image memory (not shown) provided in the signal processing unit.

Next, the wavelength selector 22 switches a wavelength of modulated light to be a predetermined wavelength $\lambda_2$, and the same measurement as described above is carried out. In the same way as above, a reconstructed image, e.g., a cross sectional image of the absorption coefficient $\mu_{a2}$ at a wavelength $\lambda_2$ is stored in a second image memory (not shown) provided in the signal processing unit 75. Further, the signal processing unit 75 processes cross sectional images at a wavelength $\lambda_1$ and a wavelength $\lambda_2$ to calculate the cross sectional image of a concentration of a specific absorptive constituent or the cross sectional image of a degree of the oxygen saturation of hemoglobin. Furthermore, these results are displayed and recorded on an image display-record unit 81.

Note that the cross sectional images obtained in the above embodiments are concentrations of the absorptive coefficient, the scattering coefficient and the degree of oxygen saturation of hemoglobin, in the scattering medium. In the above description, as the controllable known values, the modulated angular frequencies $\omega_1$ and $\omega_2$ and the wavelengths $\lambda_1$ and $\lambda_2$ are used but the number of known values can be increased or decreased in accordance with the desired measurement.

Thus, as described above, according to the present invention, light having various incident angle components is caused to be incident on a scattering medium to generate an equivalent point light source or a group of equivalent point light sources near the surface of the scattering medium and then internal information in the scattering medium is measured, so that the measurement accuracy is significantly improved and the absolute value measurement with high accuracy can be made possible. For various scattering media having different transport scattering coefficients and absorption coefficients, the position at which the equivalent light source is generated is fixed, so that the accuracy of the measurement of internal information can be significantly improved. Furthermore, the distribution of diffusion-propagation paths of the diffused and propagating light in the scattering medium on the light incident side and the photodetection side are symmetric, so that the arithmetic process for obtaining information at a specific position is simplified and its measurement accuracy is significantly improved.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application Nos. 301979/1993 filed on Dec. 1, 1993 and 83489/1994 filed on Apr. 21, 1994 are hereby incorporated by reference.

What is claimed is:

1. A method for measuring a scattering medium comprising:

emitting light having a predetermined wavelength;

causing said light to be incident on a scattering medium through a light incident point so that said light has various incident angle components at the light incident point;

detecting the light having said predetermined wavelength, diffused during propagation in said scattering medium at a photodetection point different from the light incident point to obtain an optically detected signal;

processing said optically detected signal to detect a predetermined parameter, said predetermined parameter being primary information relating to a scattering characteristic and an absorption characteristic on a diffusion-propagation path, and being selected from the group consisting of a phase delay of a signal having a predetermined modulated frequency component included in said optically detected signal, a time integral value of time-waveform of said optically detected signal, a delay time of time-waveform of said optically detected signal, a differential coefficient of time-waveform of said optically detected signal and an amplitude of a signal having a predetermined modulated frequency component included in said optically detected signal; and processing said predetermined parameter based on a relation between a scattering characteristic and an absorption characteristic corresponding to said light having said predetermined wavelength on said diffusion-propagation path, and said predetermined parameter to calculate internal information in said scattering medium, said relation being a solution of a photon diffusion equation obtained by using an assumption that light diffusion of said light starts immediately from the light incident point, said internal information being secondary information and being selected from the group consisting of an absorption coefficient, a transport scattering coefficient and an effective attenuation coefficient.

2. A method for measuring a scattering medium according to claim 1, wherein said light having said predetermined wavelength is a plurality of light beams having a plurality of wavelengths, each having a different absorption coefficient to a specific constituent of said scattering medium;

said optically detected signal is a plurality of signals obtained corresponding to said light beams;

said predetermined parameter which is the primary information is a plurality of parameters detected by processing each said optically detected signal; and said relation is a plurality of relations between a scattering characteristic and an absorptive characteristic corresponding to each said light beam having said predetermined wavelength on said diffusion-propagation path, and said predetermined parameters.

3. A method for measuring a scattering medium according to claim 1, wherein said optically detected signal is a plurality of signals obtained by detecting said light having said predetermined wavelength and diffused during propagation on said diffusion-propagation path in said scattering medium corresponding to a plurality of different distances between said light incident point and said photodetection point;

said predetermined parameter which is the primary information is a plurality of parameters detected by processing each said optically detected signal; and said relation is a plurality of relations between a scattering characteristic and an absorptive characteristic corresponding to said light having said predetermined wavelength on the diffusion-propagation path, and said predetermined parameters.

4. A method for measuring a scattering medium according to claim 1, wherein said light having said predetermined wavelength is modulated light.

5. A method for measuring a scattering medium according to claim 1, wherein said light having said predetermined wavelength is modulated light having a predetermined modulated frequency component; and said predetermined parameter which is the primary information is a phase delay of a signal having said predetermined frequency component detected by processing said optically detected signal.

6. A method for measuring a scattering medium according to claim 1, wherein said light having said predetermined wavelength is a plurality of modulated light beams having predetermined modulated frequency components which are different from each other;

said optically detected signal is a plurality of signals obtained corresponding to said plurality of modulated light beams;

said predetermined parameter which is the primary information is a plurality of phase delays of said signals having said predetermined modulated frequency components detected by processing said optically detected signals; and said relation is a plurality of relations between a scattering characteristic and an absorptive characteristic corresponding to each said modulated light beam having said predetermined modulated frequency component and said predetermined wavelength on the diffusion-propagation path, and said predetermined parameters.

7. A method for measuring a scattering medium according to claim 1, wherein said predetermined parameter which is the primary information is a time integral value of time-waveform of said optically detected signal.

8. A method for measuring a scattering medium according to claim 1, wherein said predetermined parameter which is the primary information is a delay time of time-waveform of said optically detected signal.

9. A method for measuring a scattering medium according to claim 1, wherein said predetermined parameter which is the primary information is a differential coefficient of time-waveform of said optically detected signal.

10. A method for measuring a scattering medium according to claim 1, wherein said light having said predetermined wavelength is modulated light having a predetermined modulated frequency component, and said predetermined parameter which is the primary information is an amplitude of a signal having the same frequency component as that of said modulated light, included in said optically detected signals.

11. A method for measuring a scattering medium according to claim 1, wherein said light having said predetermined wavelength is a plurality of modulated light beams having predetermined modulated frequency components which are different from each other;

said optically detected signal is a plurality of signals obtained corresponding to said plurality of modulated light beams;

said predetermined parameter which is the primary information is a plurality of amplitudes of signals having said predetermined modulated frequency components detected by processing said optically detected signals; and said relation is a plurality of relations between a scattering characteristic and an absorptive characteristic corresponding to each said modulated light beam having said predetermined modulated frequency component and said predetermined wavelength on the diffusion-propagation path, and said predetermined parameters.

12. A method for measuring a scattering medium according to claim 1, wherein said relation is represented by an equation derived from the following equation:

$$\phi(\rho,z,t) = c(4\pi cDt)^{-3/2} \exp(-c\mu_a t) \times$$
$$\{\exp[-(z^2 + \rho^2)/(4cDt)] - \exp[-((z + 2z_0)^2 + \rho^2)/(4cDt)]\}$$

where $\phi$ represents photon fluence rate, $\rho$ represents distance between light incident point and photodetection point, z represents position, t represents time, c represents speed of light, D represents diffusion coefficient$=[3(\mu_a+\mu_s')]^{-1}=(3\mu_{tr})^{-1}$, $\mu_a$ represents absorption coefficient, $\mu_s'$ represents transport scattering coefficient, $\mu_{tr}$ represents transport attenuation coefficient, and $z_0=0.7104/\mu_{tr}=2.1312$ D.

13. A method for measuring a scattering medium according to claim 1, wherein said relation is represented by an equation selected from the group consisting of the following equations:

$$J_g = (4\pi cD)^{3/2} z_0 t^{-5/2} \exp\{-q^2/(4cDt) - c\mu_a t\}$$

$$J_\phi = (1/2)c(4\pi cDt)^{-3/2}\exp(-c\mu_a t) \times \{\exp[-\rho^2/(4cDt)] - \exp(-q^2/(4cDt))\}$$

$$<t> = c\left[\int_0^\infty tJ(\rho,t)dt\right] / \left(\int_0^\infty J(\rho,t)dt\right)$$

$$= [1/(2D)] \cdot [q^2/(1 + q\mu_{eff})]$$

$$I_g = [1/(2\pi)] \cdot (z_0/q^3)(q\mu_{eff} + 1)\exp(-q\mu_{eff})$$
$$I\phi = [1/4\pi z_0]\{(1/\rho)\exp(-\rho\mu_{eff}) - (1/q)\exp(-q\mu_{eff})\}$$

$$\Phi_g(\omega) = (q\mu_{eff}/\sqrt{2})[(1 + \tan^2\theta)^{1/2} - 1]^{1/2} -$$
$$\tan^{-1}\{q\mu_{eff}\tan(\theta/2)/(q\mu_{eff} + [1 - \tan^2(\theta/2)]^{1/2})\}$$

and $$\Phi_\phi(\omega) = (\rho\mu_{eff}/\sqrt{2})[(1 + \tan^2\theta)^{1/2} - 1]^{1/2} -$$
$$\tan^{-1}\{\rho\mu_{eff}\tan(\theta/2)/(\rho\mu_{eff} + [1 - \tan^2(\theta/2)]^{1/2})\}$$

where

J represents photon current density, g represents mean cosine $\theta$ of the scattering angle $\theta$.

c represents speed of light,

D represents diffusion coefficient,$=[3(\mu_a+\mu_s')]^{-1}=(3\mu_{tr})^{-1}$, $\mu_a$ represents absorption coefficient, $\mu_s'$ represents transport scattering coefficient, $\mu_{tr}$ represents transport attenuation coefficient, $z_0=0.7104/\mu_{tr}=2.1312$ D, t represents time, $q^2=\rho^2+(2z_0)^2$, $\rho$ represents distance between light incident point and photodetection point, $\phi$ represents photon fluence rate, $<L>$ represents average optical pathlength=$c<t>$ $<t>$ represents mean delay time of temporal waveform of photon current or the mean time of photon flight, $\mu_{eff}$ represents effective attenuation coefficient=$[\mu_a/D]^{1/2}$, I represents time integral value of photon current density, $\Phi$ represents phase delay of Fourier transform $F(\omega)$ of photon current density, $\omega$ represents angular frequency of a modulated component of incident light, and $\theta=\tan^{-1}(\omega/c\mu_a)$.

14. A method for measuring a scattering medium according to claim 1, wherein said relation is represented by an equation derived from the following equation;

$$\phi(\rho,z,t) = c(4\pi cDt)^{-3/2} \exp(-\rho^2/(4cDt) - c\mu_a t) \times$$
$$\{\exp(-z^2/(4cDt)) - \exp(-(z + 2z_0)^2/(4cDt)) +$$
$$\exp(-(z - 2d - 4z_0)^2/(4cDt)) - \exp(-(z - 2d - 2z_0)^2/(4cDt)) +$$
$$\exp(-(z + 2d - 4z_0)^2/(4cDt)) - \exp(-(z + 2d + 6z_0)^2/(4cDt)) +$$
$$\exp(-(z - 4d - 8z_0)^2/(4cDt)) - \exp(-(z - 4d - 6z_0)^2/(4cDt))\}$$

where $\phi$ represents photon fluence rate, $\rho$ represents distance between light incident point and photodetection point, z represents position, t represents time, c represents speed of light, D represents diffusion coefficient=$[3(\mu_a+\mu_s')]^{-1}=(3\mu_{tr})^{-1}$, $\mu_a$ represents absorption coefficient, $\mu_s'$ represents transport scattering coefficient, $\mu_{tr}$ represents transport attenuation coefficient, and $z_0=0.7104/\mu_{tr}=2.1312$ D.

15. A method for measuring a scattering medium according to claim 1, wherein said relation is represented by an equation selected from the group consisting of the following equations:

$$J_z = (1/2)(4\pi cD)^{-3/2}t^{-5/2}\exp\{-c\mu_a t\} \times$$
$$\{d \exp[-d^2/(4cDt)] - (d + 4z_0)\exp(-(d + 4z_0)^2/(4cDt))\}$$

$$J_\phi = (1/2)c(4\pi cDt)^{-3/2}\exp\{-c\mu_a t\} \times$$
$$\{\exp[-d^2/(4cDt)] - 2\exp(-(d + 2z_0)^2/(4cDt)) +$$
$$\exp(-(d + 4z_0)^2/(4cDt))\}$$

$$<L> = [1/(2D)] \cdot [d^2/(1 + d\mu_{eff})]$$
$$I_z = [1/(4\pi d^2)]\exp(-d\mu_{eff}) \times \{(d\mu_{eff} + 1) -$$
$$[((d + 4z_0)\mu_{eff} + 1)/(1 + (4z_0/d))^2] \cdot \exp(-4z_0\mu_{eff})$$

$$I_\phi = [1/(4\pi z_0)] \cdot \{(1/d)\exp(-d\mu_{eff}) -$$  (3.17)
$$[2/(d + 2z_0)]\exp(-(d + 2z_0)\mu_{eff}) +$$
$$[1/(d + 4z_0)]\exp(-(d + 4z_0)\mu_{eff})\}$$

$$\Phi_g(\omega) = (d\mu_{eff}/\sqrt{2})[(1 + \tan^2\theta)^{1/2} - 1]^{1/2} + \alpha_3$$  (3.18)

and $$\Phi_\phi(\omega) = (d\mu_{eff}/\sqrt{2})[(1 + \tan^2\theta)^{1/2} - 1]^{1/2} + \alpha_4$$  (3.19)

where

J represents photon current density, g represents mean cosine $\theta$ of the scattering angle $\theta$, c represents speed of light, D represents diffusion coefficient=$[3(\mu_a+\mu_s')]^{-1}=(3\mu_{tr})^{-1}$, $\mu_a$ represents absorption coefficient, $\mu_s'$ represents transport scattering coefficient, $\mu_{tr}$ represents transport attenuation coefficient, $z_0=0.7104/\mu_{tr}=2.1312$ D, t represents time, $q^2=\rho^2+(2z_0)^2$, $\rho$ and d each represent distance between light incident point and photodetection point, $\phi$ represents photon fluence rate, <L> represents average optical pathlength=c<t>

<t> represents mean delay time of temporal waveform of photon current or the mean time of photon flight, $\mu_{eff}$ represents effective attenuation coefficient=$[\mu_a/D]^{1/2}$, I represents time integral value of photon current density, $\Phi$ represents phase delay of Fourier transform F($\omega$) of photon current density, $\omega$ represents angular frequency of a modulated component of incident light, $\theta=\tan^{-1}(\omega/c\mu_a)$, $\alpha_3=-\tan^{-1}\{(1+\exp(-2z_0\mu_{eff}))\tan(\theta/2)\}$, and $\alpha_4=-\tan^{-1}\{(\theta/2)(4z_0\mu_{eff}/(\exp(2z_0\mu_{eff})-1))\}$.

16. An apparatus for measuring a scattering medium comprising:

a light source for emitting light having a predetermined wavelength;

light-incident means for causing said light to be incident on a scattering medium through a light incident point so that said light has simultaneous multiple angles of incidence various incident angle components at the light incident point;

photodetecting means for detecting said light having said predetermined wavelength diffused during propagation in said scattering medium at a photodetecting point different from the light incident point to obtain an optically detected signal;

parameter arithmetic processing means for processing said optically detected signal to detect a predetermined parameter, said predetermined parameter being primary information relating to a scattering characteristic and an absorption characteristic on a diffusion-propagation path, and being selected from the group consisting of a phase delay of a signal having a predetermined modulated frequency component included in said optically detected signal, a time integral value of time-waveform of said optically detected signal, a delay time of time-waveform of said optically detected signal, a differential coefficient of time-waveform of said optically detected signal and an amplitude of a signal having a predetermined modulated frequency component included in said optically detected signal; and internal information arithmetic processing means for processing said predetermined parameter, on assumption that said light is diffused immediately after incidence from the light incident point, based on a relation between a scattering characteristic and an absorption characteristic corresponding to said light having said predetermined wavelength on said diffusion-propagation path, and said predetermined parameter to calculate internal information in said scattering medium, said relation being a solution of a photon diffusion equation obtained by using an assumption that light diffusion of said light starts immediately from the light incident point, said internal information being secondary information and being selected from the group consisting of an absorption coefficient, a transport scattering coefficient and an effective attenuation coefficient.

17. An apparatus for measuring a scattering medium according to claim 16, wherein said light source generates a plurality of light beams having a plurality of wavelengths, each having a different absorption coefficient to a specific constituent in said scattering medium;

said photodetecting means obtains said optically detected signal which is a plurality of signals obtained corresponding to of said light beams;

said parameter processing means processes each said optically detected signal to detect a plurality of parameters as said predetermined parameter which is the primary information; and said internal information arithmetic processing means processes said parameters based on a plurality of relations between a scattering characteristic and an absorption characteristic corresponding to each said light beam having said predetermined wavelength on said diffusion-propagation path, and said predetermined parameters to calculate internal information which is the secondary information in said scattering medium.

18. An apparatus for measuring a scattering medium according to claim 13, wherein said light-incident means and said photodetecting means are placed so that distances between light-incident points and photodetection points are different from each other;

said photodetecting means detects each said light having said predetermined wavelength diffused during propagation on the diffusion-propagation path in said scattering medium corresponding to each said distance between said light-incident point and said photodetection point to obtain a plurality of optically detected signals;

said parameter arithmetic processing means processes each said optically detected signal to detect a plurality of parameters as said predetermined parameter which is primary information; and said internal information arithmetic processing means processes said predetermined parameters based on a plurality of relations between a scattering characteristic and an absorption characteristic corresponding to said light having said predetermined wavelength on said diffusion-propagation path, and said predetermined parameters to calculate internal information which is the secondary information in said scattering medium.

19. An apparatus for measuring a scattering medium according to claim 16, wherein said light source is a light source for generating modulated light having a predetermined wavelength.

20. An apparatus for measuring a scattering medium according to claim 16, wherein said light source generates modulated light having a predetermined wavelength and a predetermined modulated frequency component;

said photodetecting means detects said light having said predetermined wavelength and said predetermined modulated frequency component to obtain an optically detected signal; and said parameter processing means processes said optically detected signal corresponding to said predetermined frequency component to detect a phase delay of said signal having said predetermined modulated frequency component which is the primary information.

21. An apparatus for measuring a scattering medium according to claim 16, wherein said light source generates a plurality of modulated light beams, each having a predetermined wavelength and a different predetermined modulated frequency component;

said photodetection means detects each said modulated light beam to obtain a plurality of optically detected signals;

said parameter arithmetic processing means processes each said optically detected signal to detect a plurality of phase delays of said signals having said predetermined modulated frequency components, said phase delays being the primary information; and said internal information arithmetic processing means processes said phase delays based on a plurality of relations between a scattering characteristic and an absorption characteristic corresponding to each said modulated light beam having said predetermined modulated frequency component and said predetermined wavelength on said diffusion-propagation path, and said phase delays to calculate internal information which is the secondary information in said scattering medium.

22. An apparatus for measuring a scattering medium according to claim 16, wherein said relation is represented by an equation derived from the following equation:

$$\phi(\rho,z,t) = c(4\pi cDt)^{-3/2} \exp(-c\mu_a t) \times \{\exp[-(z^2 + \rho^2)/(4cDt)] - \exp[-((z^2 + 2z_0)^2 + \rho^2)/(4cDt)]\}$$

where $\phi$ represents photon fluence rate, $\rho$ represents distance between light incident point and photodetection point, z represents position, t represents time, c represents speed of light, D represents diffusion coefficient=$[3(\mu_a+\mu_s')]^{-1}=(3\mu_{tr})^{-1}$, $\mu_a$ represents absorption coefficient, $\mu_s'$ represents transport scattering coefficient, $\mu_{tr}$ represents transport attenuation coefficient, and $z_0=0.7104/\mu_{tr}=2.1312$ D.

23. An apparatus for measuring a scattering medium according to claim 16, wherein said relation is represented by an equation selected from the group consisting of the following equations:

$$J_g = (4\pi cD)^{-3/2} z_0 t^{-5/2} \exp\{-q^2/(4cDt) - c\mu_a t\}$$

$$J_\phi = (1/2)c(4\pi cDt)^{-3/2}\exp(-c\mu_a t) \times \{\exp\{-\rho^2/(4cDt)\} - \exp(-q^2/(4cDt))\}$$

$$<L> = c\left[\int_0^\infty tJ(\rho,t)dt\right] / \left(\int_0^\infty J(\rho,t)dt\right)$$

$$= [1/(2D)] \cdot [q^2/(1+q\mu_{eff})]$$

$$I_g = [1/(2\pi)] \cdot (z_0/q^3)(q\mu_{eff} + 1)\exp(-q\mu_{eff})$$
$$I\phi = [1/4\pi z_0]\{(1/\rho)\exp(-\rho\mu_{eff}) - (1/q)\exp(-q\mu_{eff})\}$$

$$\Phi_g(\omega) = (q\mu_{eff}/\sqrt{2})[(1+\tan^2\theta)^{1/2} - 1]^{1/2} -$$
$$\tan^{-1}\{q\mu_{eff}\tan(\theta/2)/(q\mu_{eff} + [1 - \tan^2(\theta/2)]^{1/2})\}$$

and $$\Phi_\phi(\omega) = (\rho\mu_{eff}/\sqrt{2})[(1+\tan^2\theta)^{1/2} - 1]^{1/2} -$$
$$\tan^{-1}\{\rho\mu_{eff}\tan(\theta/2)/(\rho\mu_{eff} + [1 - \tan^2(\theta/2)]^{1/2})\}$$

where

J represents photon current density, g represents mean cosine $\theta$ of the scattering angle $\theta$, c represents speed of light, D represents diffusion coefficient=$[3(\mu_a+\mu_s')]^{-1}=(3\mu_{tr})^{-1}$.

$\mu_a$ represents absorption coefficient, $\mu_s'$ represents transport scattering coefficient, $\mu_{tr}$ represents transport attenuation coefficient, $z_0=0.7104/\mu_{tr}=2.1312$ D, t represents time, $q^2=\rho^2+(2z_0)^2$, $\rho$ represents distance between light incident point and photodetection point, $\phi$ represents photon fluence rate, <L> represents average optical pathlength=c<t>

<t> represents mean delay time of temporal waveform of photon current or the mean time of photon flight, $\mu_{eff}$ represents effective attenuation coefficient=$[\mu_a/D]^{1/2}$, I represents time integral value of photon current density, $\Phi$ represents phase delay of Fourier transform F($\omega$) of photon current density, $\omega$ represents angular frequency of a modulated component of incident light, and $\theta=\tan^{-1}(\omega/c\mu_a)$.

24. An apparatus for measuring a scattering medium according to claim 16, wherein said relation is represented by an equation derived from the following equation:

$$\phi(\rho,z,t) = c(4\pi cDt)^{-3/2}\exp(-\rho^2/(4cDt) - c\mu_a t) \times$$
$$\{\exp(-z^2/(4cDt)) - \exp(-(z + 2z_0)^2/(4cDt)) +$$
$$\exp(-(z - 2d - 4z_0)^2/(4cDt)) - \exp(-(z - 2d - 2z_0)^2/(4cDt)) +$$
$$\exp(-(z + 2d + 4z_0)^2/(4cDt)) - \exp(-(z + 2d + 6z_0)^2/(4cDt)) +$$
$$\exp(-(z - 4d - 8z_0)^2/(4cDt)) - \exp(-(z - 4d - 6z_0)^2/(4cDt))\}$$

where $\phi$ represents photon fluence rate,

ρ represents distance between light incident point and photodetection point, z represents position, t represents time, c represents speed of light, D represents diffusion coefficient=$[3(\mu_a+\mu_s')]^{-1}=(3\mu_{tr})^{-1}$, $\mu_a$ represents absorption coefficient, $\mu_s'$ represents transport scattering coefficient, $\mu_{tr}$ represents transport attenuation coefficient, and $z_0=0.7104/\mu_{tr}=2.1312\ D$.

25. An apparatus for measuring a scattering medium according to claim 16, wherein said relation is represented by an equation selected from the group consisting of the following equations:

$$J_g = (1/2)\ (4\pi cD)^{-3/2} t^{-5/2} \exp\{-c\mu_a t\} \times \{d \exp[-d^2/(4cDt)] - (d + 4z_0)\exp(-(d + 4z_0)^2/(4cDt))\}$$

$$J_\phi = (1/2)c(4\pi cDt)^{-3/2}\exp\{-c\mu_a t\} \times \{\exp[-d^2/(4cDt)] - 2\exp(-(d + 2z_0)^2/(4cDt)) + \exp(-(d + 4z_0)^2/(4cDt))\}$$

$$<L> = [1/(2D)] \cdot [d^2/(1 + d\mu_{eff})]$$

$$I_g = [1/(4\pi d^2)]\exp(-d\mu_{eff}) \times \{(d\mu_{eff} + 1) - [((d + 4z_0)\mu_{eff} + 1)/(1 + (4z_0/d))^2] \cdot \exp(-4z_0\mu_{eff})$$

$$I\phi = [1/(4\pi z_0)] \cdot \{(1/d)\exp(-d\mu_{eff}) - [2/(d + 2z_0)]\exp(-(d + 2z_0)\mu_{eff}) + [1/(d + 4z_0)]\exp(-(d + 4z_0)\mu_{eff})\}$$

$$\Phi_g(\omega) = (d\mu_{eff}/\sqrt{2})\ [(1 + \tan^2\theta)^{1/2} - 1]^{1/2} + \alpha_3$$

and

-continued $$\Phi_\phi(\omega) = (d\mu_{eff}/\sqrt{2})\ [(1 + \tan^2\theta)^{1/2} - 1]^{1/2} + \alpha_{40}$$

where

J represents photon current density, g represents mean cosine θ of the scattering angle θ, c represents speed of light, D represents diffusion coefficient=$[3(\mu_a+\mu_s')]^{-1}=(3\mu_{tr})^{-1}$, $\mu_a$ represents absorption coefficient, $\mu_s'$ represents transport scattering coefficient, $\mu_{tr}$ represents transport attenuation coefficient, $z_0=0.7104/\mu_{tr}=2.1312\ D$, t represents time, $q^2=\rho^2+(2z_0)^2$, ρ and d each represent distance between light incident point and photodetection point, φ represents photon fluence rate, <L> represents average optical pathlength=c<t>

<t> represents mean delay time of temporal waveform of photon current or the mean time of photon flight, $\mu_{eff}$ represents effective attenuation coefficient=$[\mu_a/D]^{1/2}$, I represents time integral value of photon current density, Φ represents phase delay of fourier transform F(ω) of photon current density, ω represents angular frequency of a modulated component of incident light, $\theta=\tan^{-1}(\omega/c\mu_a)$, $\alpha_3=-\tan^{-1}\{(1+\exp(-2z_0\mu_{eff}))\tan(\theta/2)\}$, and $\alpha_4=-\tan^{-1}\{(\theta/2)(4z_0\mu_{eff}/(\exp(2z_0\mu_{eff})-1))\}$.

\* \* \* \* \*